(12) United States Patent
Stroud

(10) Patent No.: US 9,456,589 B2
(45) Date of Patent: Oct. 4, 2016

(54) ELASMOBRANCH-REPELLING COMPOUNDS AND METHODS OF USE

(76) Inventor: Eric Matthew Stroud, Oak Ridge, NJ (US)

( * ) Notice: Subject to any disclaimer, the term of this patent is extended or adjusted under 35 U.S.C. 154(b) by 2489 days.

(21) Appl. No.: 11/922,065

(22) PCT Filed: Jun. 12, 2006

(86) PCT No.: PCT/US2006/022912
§ 371 (c)(1),
(2), (4) Date: Oct. 6, 2009

(87) PCT Pub. No.: WO2006/135876
PCT Pub. Date: Dec. 21, 2006

(65) Prior Publication Data
US 2010/0016346 A1    Jan. 21, 2010

Related U.S. Application Data

(60) Provisional application No. 60/689,652, filed on Jun. 11, 2005, provisional application No. 60/750,451, filed on Dec. 14, 2005.

(51) Int. Cl.
| | |
|---|---|
| *A01N 33/08* | (2006.01) |
| *A01N 35/00* | (2006.01) |
| *A01N 43/40* | (2006.01) |
| *A01K 79/02* | (2006.01) |
| *A01N 35/02* | (2006.01) |
| *A01N 35/04* | (2006.01) |
| *A01N 37/02* | (2006.01) |
| *A01N 37/06* | (2006.01) |
| *A01N 37/36* | (2006.01) |

(52) U.S. Cl.
CPC .............. *A01K 79/02* (2013.01); *A01N 35/02* (2013.01); *A01N 35/04* (2013.01); *A01N 37/02* (2013.01); *A01N 37/06* (2013.01); *A01N 37/36* (2013.01); *A01N 43/40* (2013.01)

(58) Field of Classification Search
CPC ...... A61K 31/11; A61K 31/12; A61K 31/19; A01N 35/02; A01N 35/04; A01N 43/40
USPC .......................... 514/566, 557, 666, 675, 332
See application file for complete search history.

(56) References Cited

U.S. PATENT DOCUMENTS

| | | | |
|---|---|---|---|
| 7,053 A | 1/1850 | Hare | |
| 2,389,719 A * | 11/1945 | Dinsley | 514/557 |
| 3,764,707 A * | 10/1973 | Habersberger | 514/779 |
| 4,340,587 A | 7/1982 | Antonik | |
| 4,490,360 A | 12/1984 | Antonik | |
| 4,548,764 A | 10/1985 | Munteanu et al. | |
| 4,602,099 A * | 7/1986 | Parker | 549/479 |
| 4,906,488 A * | 3/1990 | Pera | 426/573 |
| 4,909,941 A | 3/1990 | Poll et al. | |
| 5,134,138 A * | 7/1992 | Onoue et al. | 514/206 |
| 5,607,979 A * | 3/1997 | McCreery | 514/759 |
| 5,753,609 A * | 5/1998 | Nakatsu et al. | 512/8 |
| 5,989,323 A | 11/1999 | Taylor | |
| 6,028,118 A | 2/2000 | Dupont | |
| 6,606,963 B1 | 8/2003 | Wynne | |
| 6,716,441 B1 | 4/2004 | Osborne et al. | |
| 8,951,544 B2 | 2/2015 | Stroud | |
| 9,084,415 B2 | 7/2015 | Stroud | |
| 2007/0256623 A1 | 11/2007 | Stroud | |
| 2009/0038205 A1 | 2/2009 | Stroud | |
| 2010/0203154 A1 | 8/2010 | Stroud et al. | |

FOREIGN PATENT DOCUMENTS

| | | |
|---|---|---|
| WO | WO 2006/088793 | 8/2006 |
| WO | WO 2006/135876 | 12/2006 |

OTHER PUBLICATIONS

Sisneros et al., Surfactants as chemical shark repellents: past, present, and future, Environmental Biology of Fishes 60: 117-129,2001.*
Tester "A Summary of Research on Sharks". University of Hawaii, 1961.
Mudd, "High Performance Liquid Chromatography-mass Spectrometry in the Analysis of Semochemicals". 1990.
Trzaska, "Keeping Sharks at Bay". Critter Chemistry, Dec. 2004.
Hurley et al., "The Dogfish Scourge: Protecting Fishing Gear from Shark Attack". 1987.
Handwerk, "New Shark Repellent Uses Chemical Signals" National Geographic News, Jul. 2004.
International Search Report of International Application No. PCT/US06/05035 mailed by the International Search Authority on Jun. 14, 2006.
International Search Report of International Application No. PCT/US06/22912 mailed by the International Search Authority on Sep. 25, 2007.

* cited by examiner

*Primary Examiner* — Kevin E Weddington
(74) *Attorney, Agent, or Firm* — Hoxie & Associates LLC

(57) ABSTRACT

Compounds for repelling elasmobranch having an aldehyde or derivative, a carboxylic acid a derivative, a ketone or a derivative thereof, a di-ketone or a derivative thereof, a pyridine or derivative thereof, or an antipyrine or a derivative thereof and methods of use thereof.

15 Claims, No Drawings

ELASMOBRANCH-REPELLING COMPOUNDS AND METHODS OF USE

CROSS-REFERENCE TO RELATED APPLICATIONS

This application is a national phase application of International PCT application serial number PCT/US2006/022912 filed on Jun. 12, 2006, which claims the benefit of U.S. Provisional Application No. 60/689,652 filed on Jun. 11, 2005 and U.S. Provisional Application No. 60/750,451 filed on Dec. 14, 2005.

INTRODUCTION

This invention relates generally to gustatory elasmobranch repellents comprising aldehydes, carboxylic acids, ketones, di-ketones, pyridines and anti-pyrines, separately or in combination.

BACKGROUND OF THE INVENTION

The reality of shark (elasmobranch) attacks and a pervasive fear of shark attacks in the modern world combine to create a great need for effective shark repellents. Effective shark repellents are also needed in the commercial fishing industry.

Elasmobranchs represent a significant problem in the commercial fishing industry. Elasmobranchs are often inadvertently caught on fishing hooks and tackle directed at other more commercially valuable kinds of fish. This inadvertent catching of elasmobranchs (or other non-valued fish) is called "by-catch." As many as 100 million elasmobranchs are killed each year as by-catch. This loss of life has resulted in a real threat to several shark species. Currently, as many as 80 species of shark are considered threatened with extinction.

Further, when elasmobranchs are caught as by-catch, fishing operations receive no return on their investment since the shark is caught on a hook that might have otherwise brought in a marketable fish. Additionally, the fishing tackle on which a shark is caught often must be cut loose for the safety of those working on the fishing vessel causing a loss of both equipment and time.

Longlining is a commercial fishing method that suffers significant losses from shark by-catch. Longlining uses multiple baited individual fish hooks with leaders strung at intervals along an often very long (2-3 mile) main fishing line. Longline fishing operations routinely target swordfish and tuna. The longline hooks and bait, however, are not selective and elasmobranchs are sometimes caught in greater numbers than the intended target catch. The result is great loss of life in elasmobranchs and significant financial losses in the longline industry. Elasmobranchs cause additional losses in the longline fishing industry by scavenging marketable fish caught on longlines before the fish may be retrieved for processing. This problem also applies to the commercial trawling industry.

There has been a long-felt need for methods and devices to deter elasmobranchs from commercial fishing lines and nets. Attempts in the middle of the twentieth century were made to protect trawl nets with electric discharge devices. Nelson, "Shark Attack and Repellency Research: An Overview," Shark Repellents from the Sea ed. Bernhard Zahuranec (1983) at p. 20). Nevertheless, no commercially effective repellent has been made available for reducing shark by-catch in the commercial fishing industry or for reducing loss of valuable fish or fishing tackle to shark predation.

An effective shark repellent would not only be valuable to the fishing industry but also would be valuable for protecting humans from shark attacks. An effective repellent has yet to be marketed for limiting the risk of shark attacks faced by humans exposed to elasmobranchs. Over the last 50 years antishark measures employed to protect humans from sharks have included electrical repellent devices (Gilbert & Springer 1963, Gilbert & Gilbert 1973), acoustical playbacks (Myrberg et al. 1978, Klimley & Myrberg 1979), visual devices (Doak 1974) and chemical repellents (Tuve 1963, Clark 1974, Gruber & Zlotkin 1982). None of these procedures proved satisfactory in preventing shark attacks. (Sisneros (2001)). As such, the long felt need for an effective repellent has not been satisfied.

Researchers have historically used several bio-assays to determine if a repellent evokes a flight response in shark. One such bio-assay measures the effect of a repellent on a shark that is immobilized in "tonic immobility." Tonic immobility is a state of paralysis that typically occurs when a shark is subject to inversion of its body along the longitudinal axis. This state is called "tonic," and the shark can remain in this state for up to 15 minutes thereby allowing researchers to observe effects of repellents. After behavioral controls are established, an object or substance that has a repelling effect will awaken a shark from a tonic state. Researchers can quantify the strength of a repellent effect from these studies.

BRIEF SUMMARY OF THE INVENTION

Applicant has discovered effective chemical repellents for elasmobranchs, which appear to affect the elasmobranch's gustatory (taste) receptors. According to the present invention, an elasmobranch repellent is provided comprising an aldehyde or a derivative thereof, a carboxylic acid or a derivative thereof, a ketone or derivative thereof, a di-ketone or a derivative thereof, a pyridine or a derivative thereof, or an antipyrine or a derivative thereof, separately or in combination. When tested, these elasmobranch repellents are capable of terminating tonic immobility of a tonic-immobile elasmobranch when introduced to elasmobranch gustatory receptors.

According to a first non-limiting embodiment of the present invention, a composition for repelling an elasmobranch is provided comprising an aldehyde or a derivative thereof. In a preferred non-limiting embodiment, the composition comprises a methylbutanal. In a more preferred non-limiting embodiment, the aldehyde is selected from 3-methylbutanal or 2-methylbutanal. In another preferred non-limiting embodiment, the composition comprises methylbutenal. In a more preferred non-limiting embodiment, the aldehyde is selected from 2-methylbutenal or 3-methylbutenal.

In an alternative non-limiting preferred embodiment of the first embodiment, the aldehyde comprises a linear carbon chain of about 5 carbons. In a more preferred embodiment, the aldehyde is selected from valeraldehyde, pentanal or trans-pentenal.

In an alternative non-limiting preferred embodiment of the first embodiment, the aldehyde comprises a saturated carbon chain comprising 1 carbon to about 6 carbons. In a more preferred embodiment, the saturated aldehyde is selected from formalin (the acetal form of formaldehyde gas in water), acetaldehyde, propionaldehyde, butyraldehyde, isobutyraldehyde, valeraldehyde (pentanal), capronaldehyde (hexanal), trimethylacetaldehyde (pivic aldehyde) and isovaleraldehyde (3-methylbutanal).

In another preferred embodiment of the first embodiment, the composition for repelling an elasmobranch comprises a natural aldehyde. In a more preferred embodiment, the natural aldehyde is selected from cinnimaldehyde, cuminaldehyde and acetaldehyde. In a more preferred embodiment, the natural aldehyde is piperonal.

In another alternative preferred embodiment of the first embodiment, the composition for repelling an elasmobranch comprises an aromatic aldehyde, solubilized in a suitable polar solvent. In a more preferred embodiment, the aromatic aldehyde is selected from one or more methoxybenzaldehydes and a tolualdehyde.

In an alternative preferred non-limiting embodiment, the composition comprises a combination of two or more aldehydes or aldehyde derivatives.

According to a second non-limiting embodiment of the present invention, a composition for repelling an elasmobranch is provided comprising a carboxylic acid or a derivative thereof. In a preferred non-limiting embodiment, the composition comprises butyric acid. In another preferred non-limiting embodiment, the composition comprises citric acid. In other preferred non-limiting embodiments, the carboxylic acid is selected from trans-cinnamic acid, 2-butenoic acid, lactic acid, 2,2-dimethylbutyric acid, 2,3,3-trimethylproprionic acid, 2-ethylbutyric acid, 2-ketobutyric acid, 3-aminobutyric acid, 4-acetylbutyric acid, 3-butenoic acid, tricarballylic acid and hydroxysuccinic acid. In an alternative preferred non-limiting embodiment, the composition comprises a combination of two or more carboxylic acids or carboxylic acid derivatives. In a more preferred non-limiting embodiment, the combination of carboxylic acids comprises at least two carboxylic acids selected from crotonic acid, cinnamic acid, maleic acid, citric acid and fumaric acid. In another more preferred non-limiting embodiment, the combination comprises crotonic acid, cinnamic acid and maleic acid. In an alternative preferred non-limiting embodiment, the combination of carboxylic acids comprises crotonic acid, citric acid and fumaric acid.

In a third non-limiting embodiment of the present invention, a composition for repelling an elasmobranch is provided comprising a ketone or a derivative thereof. In a preferred non-limiting embodiment, the composition for repelling an elasmobranch comprises ionone. In another preferred non-limiting embodiment, the composition for repelling an elasmobranch comprises zingerone. In an alternative preferred non-limiting embodiment, the composition comprises a combination of two or more ketones or ketone derivatives.

In a fourth non-limiting embodiment of the present invention, a composition for repelling an elasmobranch is provided comprising a di-ketone or derivative thereof. In a preferred non-limiting embodiment, the composition for repelling an elasmobranch comprises 2,3-butanedione. In another preferred non-limiting embodiment, the composition for repelling an elasmobranch comprises glyoxal. In another preferred non-limiting embodiment, the composition for repelling an elasmobranch comprises methylglyoxal. In an alternative preferred non-limiting embodiment, the composition comprises a combination of two or more di-ketones or diketone derivatives.

In a fifth non-limiting embodiment of the present invention, a composition for repelling an elasmobranch is provided comprising a pyridine or a derivative thereof. In a preferred non-limiting embodiment, the composition for repelling an elasmobranch comprises pyridine. In another preferred embodiment, the composition for repelling an elasmobranch comprises 3-methylpyridine or 2-amino-3-picoline. In an alternative preferred non-limiting embodiment, the composition comprises a combination of two or more pyridines or pyridine derivatives.

In a sixth non-limiting embodiment of the present invention, a composition for repelling an elasmobranch is provided comprising an anti-pyrine or a derivative thereof. In a preferred non-limiting embodiment, the composition for repelling an elasmobranch comprises anti-pyrine. In another preferred embodiment, the elasmobranch repellent comprises 4-amino-antipyrine. In an alternative preferred non-limiting embodiment, the composition comprises a combination of two or more anti-pyrines or an anti-pyrine derivative.

In a non-limiting embodiment of the present invention, a composition for repelling an elasmobranch is provided comprising a combination of two or more of aldehydes or derivatives thereof, carboxylic acids or derivatives thereof, ketones or derivatives thereof, diketones or derivatives thereof pyridines or derivatives thereof or antipyrines or derivatives thereof. In a preferred non-limiting embodiment, the composition for repelling an elasmobranch comprises an aldehyde and a diketone. In a more preferred non-limiting embodiment, the composition for repelling an elasmobranch comprises butyraldehyde, isobutyraldehyde, veratraldehyde and 2,3-butanedione.

A method of repelling an elasmobranch is provided comprising administering a composition for repelling an elasmobranch comprising an aldehyde or a derivative thereof, a carboxylic acid or a derivative thereof, a ketone or a derivative thereof, a di-ketone or a derivative thereof, a pyridine or a derivative thereof, or an antipyrine or a derivative thereof, separately or in combination, in the expected proximity of said elasmobranch. In a preferred non-limiting embodiment, the composition for repelling an elasmobranch is administered from an aerosol canister. In another preferred non-limiting embodiment, the composition for repelling an elasmobranch is administered in proximity of a longline.

A method of manufacturing an elasmobranch repellent is provided comprising the steps of combining an aldehyde or a derivative thereof, a carboxylic acid or a derivative thereof, a ketone or derivative thereof, a di-ketone or a derivative thereof, a pyridine or a derivative thereof, or an antipyrine or a derivative thereof, each alone or in combination with one another or other ingredients, with an acceptable solvent, carrier, diluent or other vehicle for administration or storage prior to administration.

A kit is provided comprising a composition for repelling an elasmobranch comprising a composition for repelling an elasmobranch comprising an aldehyde or a derivative thereof, a carboxylic acid or a derivative thereof, a ketone or derivative thereof, a di-ketone or derivative thereof, a pyridine or a derivative thereof, or an antipyrine or a derivative thereof, separately or in combination, and a vehicle for administering said composition for repelling an elasmobranch. In a preferred embodiment, the kit comprises a vehicle selected from a pressurized or pressurizable delivery device, a pressurized or pressurizable repellent gun, a miniature pressurizable repellent gun to be worn on a wrist or an ankle of a subject, a spear fishing gun with an adjacent pressurizable container for said composition, a time release sponge, a surfboard, a pump delivery system affixed to a surfboard, a pressurized delivery device affixed to a surfboard, a wristwatch comprising said composition, a syringe, a pressurized syringe, an aerosol bomb, a mortar-launched aerosol bomb, a remote-controlled buoy with a repellent tank, a fixed buoy with a metering pump, a repellent pouch, a jelly comprising glycol ether and hydroxypropylcelluose, a skin lotion containing said repellent, a porous fabric impregnated with repellent, rechargeable porous fabric impregnated with said repellent, a submerged repellent mine, a repellent-impregnated cable insulation for an undersea cable, and a repellent-impregnated cable jacket for an undersea cable.

DETAILED DESCRIPTION OF THE INVENTION

"Elasmobranchii" represents the subclass of class Chondrichthyes (cartilaginous fish), which includes the sharks and rays. In this specification, "elasmobranchs" represent the super-orders and orders of elasmobranchs that are of interest for producing a repellent based on availability and conservation, and also those that present a potential threat to humans or represent a bycatch problem in commercial fisheries. As such, "elasmobranchs" in this specification means one or more elasmobranchii in the super-orders Galeomorphii and Squalomorphii and orders Squaliforms (dogfish), Carcharhiniformes (requiem sharks), Lamniformes (mackerel sharks), and Orectolobiformes (carpet sharks).

"Derivative" is a chemical compound that may be produced from a compound of a similar structure in one or more steps, as in replacement of hydrogen by an alkyl, acyl, amino group, etc, wherein the derivative has a repellent function in elasmobranchs.

"Feeding zone" is the area in which sharks have been stimulated and demonstrate aggressive feeding behavior.

"Gustatory Response" is a response in an elasmobranch to a stimulation of taste receptors.

"Solvent" is a first substance capable of dissolving another substance.

"Carrier" is a first substance capable of mixing with a second substance.

"Diluent" is a first substance capable of mixing with a second substance such that the second substance is decreased in concentration.

"Tonic immobility" is the state of paralysis that typically occurs when an elasmobranch is subject to inversion of its body along the longitudinal axis of the body, i.e., is belly up. The elasmobranch can remain in this state for up to 15 minutes.

I. COMPOSITIONS FOR REPELLING ELASMOBRANCH

The elasmobranch repellent activity of aldehydes, carboxylic acids, ketones, diketones, pyridines or antipyrines has been demonstrated in eight species of elasmobranch. Tests demonstrate the repelling compounds are correlated with a flight response in elasmobranchs wherein the flight response is correlated with stimulation of elasmobranch taste receptors with the repelling compounds. As such, these compounds were effective as elasmobranch repellents.

Flight responses upon exposure to the repelling compounds disclosed herein have been observed in bioassays of eight different species across two different orders of elasmobranch and three different families of elasmobranch including lemon sharks of various sizes and ages (*N. brevirostris*, Order Carcharhiniformes, Family Carcarhinidae), nurse sharks of various sizes and ages (*C. cirratum*, Order Orectolobiformes, Family Ginglymostomatidae), tiger sharks of various sizes and ages (*G. cuvieri*, Order Carcharhiniformes, Family Carcarhinidae) blacktip sharks of various sizes and ages (*C. limbatus* Order Carcharhiniformes), blacknose sharks of various sizes and ages (*C. acronotus*, Order Carcharhiniformes, Family Carcarhinidae), Caribbean reef sharks of various sizes and ages (*C. perezii*, Order Carcharhiniformes, Family Carcarhinidae), great hammerhead sharks (*Sphyrna mokarran*, Order Carcharhiniformes, Family Sphyrnidae), and blue sharks (*Prionace glauca*, Order Carcharhiniformes, Family Carcarhinidae).

Among the above-listed species, flight responses have repeatedly been observed upon exposure to a wide variety of different aldehydes or combinations of aldehydes from one to ten carbons in length; including methylbutanals, methylbutenals, linear five-carbon aldehydes, saturated one-to-six carbon aldehydes, unsaturated two-to-six carbon aldehydes, natural aldehydes, aromatic aldehydes, piperonal and combinations of aldehydes. Aldehydes and there derivatives are disclosed herein as effective elasmobranch repellents.

Flight responses have likewise repeatedly been observed in elasmobranchs upon exposure to an extensive variety of carboxylic acids or combinations of carboxylic acids, including butyric acid, citric acid, crotonic acid and mixtures of crotonic acid, cinnamic acid and maleic acid, and crotonic acid, citric acid and fumaric acid. Carboxylic acids and their derivatives are disclosed herein as effective elasmobranch repellents.

Flight responses have likewise repeatedly been observed in elasmobranchs upon exposure to ketones such as ionone and zingerone. Ketones and their derivatives are disclosed herein as effective elasmobranch repellents.

Flight responses have also been observed in elasmobranchs upon exposure to diketones, such as 2,3-butanedione (diacetyl). Diketones and their derivatives are disclosed herein as effective elasmobranch repellents.

Flight responses have likewise repeatedly been observed upon exposure to pyridine and pyridine derivatives such as 3-methylpyridine, 2-amino-3-picoline and upon exposure to anti-pyrines and derivatives thereof, such as 4-aminoantipyrine and antipyrine solutions. See Tables 25-26. Pyridines and their derivatives and anti-pyrines and their derivatives are disclosed herein as effective elasmobranch repellents.

Surprisingly, fish appear unresponsive to these shark-repelling aldehydes. Tests involving captive Cobia and Yellowfin Tuna show that feeding behavior is actually slightly increased in the presence of aldehydes, particularly 3-methylbutanal, a potent shark gustatory repellent. Similarly, teleost reef fish, such as Triggerfish and Snappers, have been observed feeding and swimming in a cloud of shark-repelling aldehydes. This behavior is presumed to result from the lack of aldehyde-receptors in the fishes' gustatory system. Interestingly, aldehyde dehydrogenases (ALDH, ALDH2) have been found in certain species of fish.

In open water tests, the Queen triggerfish (*Ballistes vetula*), Durgeon Triggerfish (*Melichthys niger*), Bermuda Chub (*Kyphosus sectatrix*), Yellowtail Snapper (*Ocyurus chrysurus*) and Remora (*Remora remora*) were observed to be unaffected by exposure to elasmobranch repellents in numerous tests.

Flight responses, or repellency activity, may be demonstrated in any method described herein or known to one of skill in the art. Flight responses have been observed and measured using several bioassays known in the art to correlate with flight response.

One bioassay used to observe and measure flight response is the tonic immobility test. Tonic immobility is a state of paralysis that typically occurs when a shark is subject to inversion of its body along the longitudinal axis. This state is called "tonic," and the shark can remain in this state for up to 15 minutes thereby allowing researchers to observe effects of chemical repellents. The "tonic" state of the shark is first established by releasing seawater in proximity to the "tonic" shark with the same delivery instrument and at the same distance as a "test" repellent compound will be released. Some controls are released with a high flow rate (30 mL/sec) in order to establish that sharks are not awakened by a jet of fluid over their noses. Once behavioral controls are established, a compound or composition that may have a repelling effect is delivered to the shark. If the compound or composition engenders a flight response, the shark will awaken from the tonic state and rapidly attempt to flee the delivered repellent. Using this tonic immobility bioassay researches can quantify the strength of a repellent effect.

In the tonic immobility studies disclosed herein, several different methods were employed for delivery of repelling compounds. A first method for delivery of chemical repellent in tonic immobility studies employed a "Syringe 3/5/10 Assay" method. The "Syringe 3/5/10 Assay" method is so named because a test repellent is delivered to a shark from a distance of about "3" inches with a bolus of about "5" mL with a response to the test repellent considered positive if the shark reacts with a change in behavior within less than about "10" seconds from the time of delivery.

The "3/5/10 Syringe Assay" as employed herein delivered a dose of 5-6 mL of a test chemical repellent from a syringe fixed with a needle having a gauge of about 22 from a distance at least 3 inches in front of a shark. Because the test chemical repellent was delivered at a distance from the shark's nares and mouth, a cloud of test chemical repellent was dispersed over the shark within the water column. The dispersed test repellent was subject to water current direction, dispersion and dilution. As a result, a flight response within 10 seconds was considered a positive repellency response. Time from delivery of the test substance until a response was observed, measured and recorded. Time from delivery to response is related to the size of the bolus delivered from the syringe, distance of the shark from the syringe and water current. As such, a longer time to response does not reflect reduced potency for a particular compound. To the contrary, a longer time to response as compared to some other compound or test simply demonstrates potency even after a cloud of repellent has traveled some distance against water current.

A second delivery method called the "Syringe Assay" method delivered a dose of 60 mL or more of a test chemical repellent from at least one foot, and up to as many as five feet, from a shark. The distance of delivery was determined based on the strength of the water current in the direction of the shark. Time from delivery of the test substance until response was observed, measured and recorded. The "Syringe" method allows a researcher to observe how a diffusing and diluting cloud of test chemical repellent affects the shark's behavior when the shark encounters the delivered cloud of test substance. The "Syringe" method requires relatively large doses because of the diffusion of the cloud over time and distance. Time from delivery to response is related to the size of the bolus delivered from the syringe, distance of the shark from the syringe and water current. As such, a longer time to response does not reflect reduced potency for a particular compound, as discussed above.

A third method of delivery was called the "Bite Assay." In this method of delivery, a dose of typically less than 5 mL was presented directly into a shark's mouth using a pipette.

A fourth method of delivery was called the "Micropipette Assay" method of delivery. In this method, a very small dose (fraction of a mL) of a test substance was delivered directly into a shark's mouth. The Micropipette Assay did not consistently terminate tonic immobility in most chemical tests. A response, such as a cough or other notable action of the shark, was usually noted when effective gustatory repellents were delivered directly into a shark's mouth while in tonic immobility.

The Micropipette Assay method has not proven to be a particularly effective method of assaying for a flight response in elasmobranchs. The Micropipette Assay method is, nevertheless, an excellent method for specifying that a gustatory response has occurred. It is effective for specifying a gustatory response because the micropipette delivery method allows direct delivery of an entire bolus of test substance into the mouth of the shark being tested. A combination of data from micropipette assays demonstrating a gustatory response and other assays demonstrating a flight response is an excellent combination of data demonstrating both the repellent activity of a compound and its effectiveness as a gustatory repellent.

Another bioassay used to observe a flight response in sharks is a free-swimming test using a small metal cage containing bait. This assay is referred to as a "Cage Assay." The cage with bait is suspended below a float in the water column. A ⅜ inch diptube is secured from the cage to the boat and carried chemical compounds to the proximity of the cage where the test substances were delivered. Sharks are drawn to the vicinity of the boat with chum. Sharks are observed to immediately bump and bite at the cage wherein bait was contained. The number of interactions between the sharks and the cage are recorded over time. Test chemical repelling substance is delivered to the vicinity of the cage through the diptube. The frequency of bumps and strikes by sharks against the cage is then monitored and recorded. If bumps and strikes by sharks cease for a period of time, that time period is also recorded. In the free-swim ring tests disclosed herein using a baited cage, the volume of test chemical repellent delivered into the vicinity of the cage was about 500 mL.

Another bioassay used to observe a flight response in sharks is a cloud dispersion assay on competitively feeding population of sharks. This assay is referred to as a "Cloud Dispersion Assay" or "Cloud Assay." A pressurized fluid delivery system was designed to deliver repellent into large feeding populations of sharks. The repellent is released as a subsurface cloud, which follows the current. A 1 L plastic container containing the test chemical repellent solution is pressurized to approximately 20 psig with a battery compressor or hand pump. A globe valve is used to hold back the fluid. The fluid is delivered to the end of a long PVC pole using a Teflon tubing. This allows the operator to place the tip of the pole well into a population of feeding sharks. By actuating the small globe valve, a cloud of the chemical solution is released quickly and reliably into the feeding population. Controls are established using FD&C Red 40 dye and seawater, uncolored seawater, and air. These controls establish that sharks are not afraid to approach the delivery pole, nor are sharks deterred from feeding by the jet of control fluid or air.

A. Composition for Repelling Elasmobranchs Via Gustatory Receptors

Compositions for repelling an elasmobranch via said elasmobranch's gustatory receptors are disclosed herein. Gustatory repellent compositions may comprise an aldehyde or a derivative thereof, a carboxylic acid or a derivative thereof, a ketone or derivative thereof, a di-ketone or derivative thereof, a pyridine or a derivative thereof or an antipyrine or a derivative thereof, or any compound that terminates tonic immobility or otherwise evokes a behavioral response when administered to the mouth of an elasmobranch in tonic immobility.

The biological activity of a gustatory chemical shark repellent differs from olfactory and respiratory repellents. This is readily observed using the tonic immobility bioassay. Unlike mammals, a shark's "nose" (olfactory system) is isolated from its mouth, but its mouth and gills are interrelated.

Using a microliter syringe or microliter pipette, a bolus of test chemical can be directed precisely into one of the shark's nares, or its mouth. Gustatory repellents will terminate tonic immobility or evoke a behavioral response from a "tonic" shark almost immediately when injected into the mouth of the shark. Olfactory repellents will terminate tonic immobility almost immediately when injected into a nare of the shark.

Repellents that act upon the respiratory system, such as surfactants, saponins, and soaps, are typically introduced in the mouth, but a delayed coughing response is observed. The delayed response generally occurs after two gill pumps following the introduction of the test compound into the shark's mouth.

Gustatory repellent compounds typically will cause the shark to lock its mouth wide open, followed by head shaking. Respiratory repellent compounds will invoke coughing and violent gill pumping responses as the chemical contacts the gill rakes through pumping action.

During chemical repellent tests, a divider may be used to control the flow of trace amount of test chemical. A thin strip of plastic may be placed between the shark's mouth and nares, to minimize any chances that an olfaction substance will enter the mouth, or that a gustation compound will enter the nares. While the mouth may be separated from the nose in shark investigations, there is no way to segregate the gills from the shark's "palate" within the mouth. It has been hypothesized that the insertion of some kind of internal dam into the mouth might separate the "palate" from the gills but it is expected that this would injure the animal and, as such, would be an unsatisfactory research method.

Gustatory responses have been demonstrated in seven species of shark (lemon, nurse, blacktip, tiger, blacknose, Caribbean and blue) in a wide range of aldehydes and aldehyde mixtures; including methylbutanals, methylbutenals, linear five-carbon aldehydes, saturated one-to-six carbon aldehydes, unsaturated two-to-six carbon aldehydes, natural aldehydes, aromatic aldehydes, aldehydes of up to ten carbons in length and in combinations of aldehydes. See Tables 14-23. In Tables 14-23, results of tests using aldehyde and combinations of aldehydes on different species of elasmobranch are provided. Of particular interest for the differentiation of a gustatory response from an olfactory response are the tonic immobility assays using a micropipette delivery method wherein chemical repellent is delivered directly into the mouth of the test shark. A gustatory response is positive when tonic immobility is terminated and a flight response is observed (denoted under column "T?" as "Y") or when a change in shark behavior short of termination of tonic immobility is observed, such as a cough (denoted under column "T?" as "R"). "N" under column "T?" denotes no response.

Gustatory responses to aldehydes and aldehyde mixtures are likewise confirmed in Tables 1-8 using the delivery methods (other than "micropipette") that resulted in termination of tonic immobility or change of behavior. A review of the data in Tables 14-23 reveals that delivery of aldehydes or combinations of aldehydes directly to the mouth of a shark using a micropipette terminated tonic immobility in numerous tests among several different species of shark. Delivery of aldehydes or combinations of aldehydes directly to the mouth of nurse sharks in bite tests likewise resulted in termination of tonic immobility.

From the data presented herein, it is believed that a gustatory response (response based on detection of the repellent in the mouth) is different from an olfactory response (a response based on detection of the repellent in nares). Of particular interest for the differentiation of a gustatory response from an olfactory response are tonic immobility assays using a micropipette delivery method wherein chemical repellent is delivered directly into the mouth of the test shark. A gustatory response is positive when tonic immobility is terminated and a flight response is observed. See Tables 14-27.

The data in Tables 14-23 evidences that aldehydes stimulate gustatory receptors in creating a flight response. Gustatory responses have likewise repeatedly been observed upon exposure to pyridine and pyridine derivatives such as 3-methylpyridine, 2-amino-3-picoline as well as upon exposure to 4-aminoantipyrine and antipyrine solutions. See Tables 25-26. In Tables 25 and 26, results of tests using pyridine and antipyrine derivatives on different species of elasmobranch are provided. While delivery of about 500 microliters of pyridine from a micropipette directly into the mouth of a nurse shark did not evoke a response, "Syringe 3/5/10" assays and "Hd syringe" assays, which provide a stream of test substance to the mouth and nares of a shark, predominantly terminated tonic immobility. Delivery of 400 microliters of antipyrine solution from a micropipette evoked a response in one assay and did not evoke a response in another. "Hd Syringe" assays, which direct a precise bolus of test substance to the mouth and nose of a shark, with 4-aminoantipyrine terminated tonic immobility in all tests.

The data in Tables 25-26 evidence that pyridines and pyridine derivatives and antipyrines and antipyrine derivatives stimulate gustatory receptors in creating a flight response. The data in Table 27 and Example 5 evidence that ketones and di-ketones simulate gustatory receptors in creating a flight response.

B. Composition for Repelling Elasmobranchs Comprising Aldehydes

A composition for repelling an elasmobranch may comprise an aldehyde or a derivative thereof. Tables 1-7 and examples 1-8 and 12 provide data evidencing repeated observation of flight responses among seven species of elasmobranch upon exposure to more than twenty different aldehydes or combinations of aldehydes from one to ten carbons in length; including methylbutanals, methylbutenals, linear five-carbon aldehydes, saturated one-to-six carbon aldehydes, unsaturated two-to-six carbon aldehydes, natural aldehydes, aromatic aldehydes and combinations of aldehydes.

Exemplary and non-limiting aldehydes disclosed herein as elasmobranch repellents include, and are not limited to, 3-methylbutanal, 2-methylbutanal, 3-methylbutenal, 2-methylbutenal, valeraldehyde, trans-pentenal, propionaldehyde, butyraldehyde, isobutyraldehyde, capronaldehyde (hexanal), trimethylacetaldehyde (pivaldehyde or pivic aldehyde), trans-cinimaldehyde, cuminaldehyde, piperonal, methoxybenzaldehydes, vanillin, 2-ethylbutyraldehyde (diethylacetaldehyde), iso-butyraldehyde (2-methylpropionaldehyde), heptanal (heptyl aldehyde), octanal (octyl aldehyde), nonanal (nonyl aldehyde), decanal (decyl aldehyde), dimethylbenzaldehydes, o-anisaldehyde, m-anisaldehyde and p-anisaldehyde.

In general, the aldehyde function appears to be a tremendously powerful gustatory compound. In humans, aldehydes such as cuminal invoke spicy flavors, e.g., benzaldhyde (cherries), piperonal (black cherries), cinnimal (hot cinnamon), etc. However, in a shark, these receptors, if they exist, may invoke entirely different sensations. It is reasonable to expect that a shark would never encounter a free-aldehyde in the ocean, particularly aldehydes of C2-C6, and therefore would find them distasteful.

Most aldehydes having carbon chains of more than four carbons are not water soluble. In these cases, denatured alcohol may be used to solubilize the aldehyde. A preferred solvent may be a mixture of methanol and ethanol. A more preferred solvent may be a 50% w/w mixture of methanol and ethanol, denatured ethanol, or diethylene glycol monoethyl ether.

The electrophilic carbonyl function of the aldehyde makes it fairly reactive. If the aldehyde is soluble enough in seawater, which is slightly basic, cyclic addition products may be reversibly formed. These products are called "cyclic acetals" or simply "acetals." Because acetyls of the aldehydes disclosed herein likely form when the aldehydes are exposed to water, acetals of the aldehydes disclosed herein are also expected to play a role in gustatory repelling of elasmobranchs.

1. Methylbutanals

Methylbutanals may be administered to elasmobranchs as a repellent, including methylbutanal or any derivative thereof. Excellent gustatory repellent activity has been observed in 3-methylbutanal and 2-methylbutanal as demonstrated in Table 1.

Table 1, which summarizes the data in Tables 14 and 15, evidences the gustatory repellent characteristics of methylbutanals. In 35 of 36 assays (combining columns "Y" and "R" under the column labeled "Total (Not including Micropipette Assays)" to arrive at a 97% effectiveness rate), including assays on lemon, nurse, tiger and blacktip sharks, the gustatory repellent activity of 3-methylbutanal was established. In 81% of assays, tonic immobility was fully terminated. Termination of tonic immobility demonstrates a flight response and good repellent activity. In 17% of assays, a behavioral change was observed in the shark being tested even though the shark remained paralyzed in tonic immobility. In only a single assay did a shark not respond to treatment with 3-methylbutanal.

In five of five assays for repellent effect of 2-methylbutanal in lemon and nurse sharks, tonic immobility was terminated with as little as 200 microliters of repellent.

Together the data in Table 1 evidence the effectiveness of methylbutanals as elasmobranch repellents. The acetyls of the methylbutanals that are created when the methylbutanals are exposed to water are also expected to play a role in the repellent activity of the methylbutanals. Methylbutanals may be administered into the vicinity of an elasmobranch in a method known in the art or herein disclosed.

The methylbutanal compounds, 3-methylbutanal and 2-methylbutanal, are preferred elasmobranch repellents because they are not prohibited by federal regulations, are easy to handle, and provide a very strong repellent response. Other derivatives of the methylbutanals including addition products, and hydroxy- or amino-substituted methylbutanals are also expected to provide good repellent effect because of the hydrogen bonding and polarity provided by such groups.

2. Methylbutenals

Methylbutenals likewise may be administered to elasmobranchs as an effective repellent, including methylbutenals or any derivative thereof. Excellent repellent activity has been observed in 2-methylbutenal and 3-methylbutenal.

TABLE 1

| Compound | Hd-Syringe | | | Syringe 3/5/10 | | | Bite | | | Total (Not including Micropipette assays) | | |
| --- | --- | --- | --- | --- | --- | --- | --- | --- | --- | --- | --- | --- |
| | Y | R | N | Y | R | N | Y | R | N | Y | R | N |
| 2-methylbutanal | 5/5 | | | | | | | | | 5/5 | | |
| 3-methylbutanal | 20/27 | 6/27 | 1/27 | 7/7 | | | 2/2 | | | 29/36 (81%) | 6/36 (17%) | 1/36 (3%) |
| Total | 25/32 | 6/32 | 1/32 | 7/7 | | | 2/2 | | | 34/41 | 6/41 | 1/41 |
| Percent of Methylbutanals Trials | 78% | 19% | 3% | 100% | | | 100% | | | 83% | 15% | 2% |

"Y" denotes termination of tonic immobility.
"R" denotes a behavior response within tonic immobility.
"N" denotes no response.

TABLE 2

|  | Hd-Syringe | | |
| --- | --- | --- | --- |
| Compound | Y | R | N |
| 2-methylbutenal | 4/4 | | |
| 3-methylbutenal | 4/4 | | |
| Total | 8/8 | | |
| Percent of Trials | 100% | | |

"Y" denotes termination of tonic immobility.
"R" denotes a behavior response within tonic immobility.
"N" denotes no response.

Table 2, which summarizes data from Tables 16 and 17, evidences the effective repellent characteristics of methylbutenals. In four of four trials for 2-methylbutenal (with volumes as low as 300 microliters) and in four of four trials for 3-methylbutenal (with volumes as low as 350 microliters), all tests on nurse and lemon sharks terminated tonic immobility. This data demonstrates the effective repellent activity of the methylbutenals. Additionally, as may be seen in Table 17, Micropipette assays demonstrate the gustatory repellent nature of the methylbutenals by showing a response to repellent directed solely to the mouth and not including the nares. Acetyl derivatives of methylbutenals are also expected to play a role in the repellent effect of the methylbutenals.

Methylbutenals may be administered into the vicinity of an elasmobranch in any method of delivery known in the art or herein disclosed. Methylbutenals are preferred elasmobranch repellents because they are not prohibited by federal regulations, are easy to handle and provide a very strong repellent response. Derivatives of methylbutenals including its addition products, and hydroxy- or amino-substituted methylbutenals are also expected to provide good repellent effect.

3. Linear 5-Carbon Aldehydes

It is demonstrated herein that aldehydes having a linear five carbon chain may be administered to elasmobranchs as a particularly effective repellent. Linear five carbon chain aldehydes are generally soluble in water and evoke a flight response in a wide range of shark species. Five carbon chain aldehydes include, methylbutanals or any derivative thereof, methylbutenals or any derivative thereof, valeraldehyde or any derivative thereof and trans-pentenal or any derivative thereof, such as pentenal. Effective repellent activity has been observed in each of these compounds.

Table 3, in combination with Tables 1 and 2 above, provides data evidencing the gustatory repellent characteristics of linear 5 carbon aldehydes. As established above methylbutanals and methylbutenals are effective elasmobranch repellents. See Tables 1-2.

TABLE 3

| | Hd-Syringe | | | Syringe | | | Total (Not including Micropipette assays) | | |
| --- | --- | --- | --- | --- | --- | --- | --- | --- | --- |
| Compound | Y | R | N | Y | R | N | Y | R | N |
| Valeraldehyde | 5/5 | | | 1/1 | | | 6/6 | | |
| Trans-pentenal | 5/5 | | | | | | 5/5 | | |
| Total | 10/10 | | | 1/1 | | | 11/11 | | |
| Percent | 100% | | | 100% | | | 100% | | |

"Y" denotes termination of tonic immobility.
"R" denotes a behavior response within tonic immobility.
"N" denotes no response.

Table 3, which summarizes data in Table 18, provides data evidencing the repellent activity of valeraldehyde and trans-pentenal. In six of six assays on lemon and nurse sharks using valeraldehyde, tonic immobility was terminated. Further, the results of micropipette assays in Table 18 using valeraldehyde support the conclusion that valeraldehyde is a gustatory repellent because all Micropipette assays showed a response by the shark to direct delivery of valeraldehyde to the mouth. Additionally, in five of five assays, trans-pentenal terminated tonic immobility in lemon and nurse sharks. Again, the results of micropipette assays in Table 18 support the conclusion that trans-pentenal is an effective gustatory repellent.

Together, the data in Tables 1, 2 and 3 establish the effectiveness of linear 5 carbon aldehydes as elasmobranch repellents. Linear 5 carbon aldehydes may be administered into the vicinity of an elasmobranch in any method of delivery known in the art or herein disclosed. As such, a composition for repelling an elasmobranch comprising a linear 5 carbon aldehyde including valeraldehyde or pentenal or trans-pentanal has been provided herein.

4. Saturated C1-C6 Aldehydes

It is demonstrated herein that aldehydes having a saturated carbon chain comprising 1 carbon to about 6 carbons may be administered to elasmobranchs as a particularly effective repellent. Such aldehydes are generally soluble in water and evoke a flight response in a wide range of shark species. Saturated 1 carbon to 6 carbon aldehydes include, formalin, acetaldehyde, proprionaldehyde, butyraldehyde, isobutyraldehyde, valeraldehyde, capronaldehyde, trimethylacetaldehyde, 3-methylbutanal or any derivative of any of the before-listed compounds. Good repellent activity has been observed in each of these compounds.

Table 4, which summarizes data from Tables 14 and 19, establishes the repellent activity of saturated C1-C6 aldehydes.

TABLE 4

| | Hd-Syringe | | | Syringe | | Bite | Total (Not including Micropipette assays) | | |
| --- | --- | --- | --- | --- | --- | --- | --- | --- | --- |
| Compound | Y | R | N | Y | N | Y | Y | R | N |
| Propionaldehyde | | | | 4/4 | | | 4/4 | | |
| Butyraldehyde | | | | 4/4 | | | 4/4 | | |
| Isobutyraldehyde | | | | 4/4 | | | 4/4 | | |
| Valeraldehyde | 5/5 | | | 1/1 | | | 6/6 | | |
| Capronaldehyde | | | | 1/1 | | | 1/1 | | |
| Trimethylacetaldehyde (pivaldehyde) | 5/5 | | | 1/2 | 1/2 | | 6/7 | | 1/7 |

TABLE 4-continued

|  | Hd-Syringe | | | Syringe | | Bite | Total (Not including Micropipette assays) | | |
| --- | --- | --- | --- | --- | --- | --- | --- | --- | --- |
| Compound | Y | R | N | Y | N | Y | Y | R | N |
| 3-methylbutanal (Isovaleraldehyde) | 20/27 | 6/27 | 1/27 | 7/7 | | 2/2 | 29/36 | 6/36 | 1/36 |
| Total | 30/37 | 6/37 | 1/37 | 22/23 | 1/23 | 2/2 | 53/61 | 53/61 | 1/61 |
| Percent of Trials | 81% | 16% | 3% | 96% | 4% | 100% | 87% | 10% | 16% |

"Y" denotes termination of tonic immobility.
"R" denotes a behavior response within tonic immobility.
"N" denotes no response.

As may be seen above, in 100% of assays performed using proprionaldehyde, butyraldehyde, isobutyraldehyde, valeraldehyde, capronaldehyde, and trimethylaldehyde, tonic immobility was terminated. These tests were done on nurse and lemon sharks. As was discussed above and shown in Table 1,3-methylbutanal is an excellent gustatory repellent.

The data in Table 4 evidences the utility of aldehydes having a saturated carbon chain comprising 1 carbon to about 6 carbons including propionaldehyde, butyraldehyde, isobutyraldehyde, valeraldehyde, capronaldehyde, trimethylacetaldehyde and 3-methylbutanal or derivatives of any of these compounds. Such aldehydes may be administered into the vicinity of an elasmobranch in any method of delivery known in the art or herein disclosed. Similarly, formalin and acetaldehyde are very water soluble and would be expected to produce similar gustation responses as the other C1-C6 aldehydes. As such, a composition for repelling an elasmobranch comprising a saturated aldehyde with a one to six carbon chain has been provided herein.

5. Unsaturated C2-C6 Aldehyde

It is demonstrated herein that aldehydes that are soluble in water and have an unsaturated carbon chain of two to six carbons may be administered to elasmobranchs as a particularly effective repellent. Unsaturated C2-C6 aldehydes include pentenal, 2-methylbutenal, 3-methyl-butenal, or any derivative of any of the before-listed compounds. Excellent repellent activity has been observed in each of these compounds.

Table 5 provides data establishing the repellent activity of unsaturated C2-C6 aldehydes. The data for pentenal, 2-methylbutenal and 3-methylbutenal is repeated from Tables 2 and 3 above.

TABLE 5

|  | Hd-Syringe | | |
| --- | --- | --- | --- |
| Compound | Y | R | N |
| Pentenal | 5/5 | | |
| 2-Methylbutenal | 4/4 | | |
| 3-Methylbutenal | 4/4 | | |
| Total | 13/13 | | |
| Percent of Trials | 100% | | |

"Y" denotes termination of tonic immobility.
"R" denotes a behavior response within tonic immobility.
"N" denotes no response.

The unsaturated aldehydes crotonaldehyde and acrolein fall within the family of unsaturated C2-C6 aldehydes and are also expected to act as gustatory repellents. The oxidize form of crotonaldehyde (crotonic acid) was shown to act as a gustatory repellent. The hydrogenated form of acrolein (propionaldehyde) was also shown to act as a gustatory repellent. Nevertheless, crotonaldehyde and acrolein are very toxic and are considered marine pollutants. As a result, testing of these compounds was not considered feasible. Further, while these compounds would be considered to be gustatory elasmobranch repellents as evidenced by the data contained herein, crotonaldehyde and acrolein are not preferred repellents.

The excellent elasmobranch repelling characteristics of pentenal, 2-methylbutenal and 3-methylbutenal is illustrated above. See Table 2.

The data in Table 5 evidences the utility of unsaturated C2-C6 aldehydes including pentenal, 2-methylbutenal and 3-methylbutenal. Such aldehydes may be administered into the vicinity of an elasmobranch in any method of delivery known in the art or herein disclosed. As such, a composition for repelling an elasmobranch comprising an unsaturated C2-C6 aldehyde has been provided herein.

6. Natural Aldehydes

It is demonstrated herein that naturally occurring aldehydes such as cinnimaldehyde, cuminaldehyde and piperonal or any derivatives of any of the before-listed compounds may be administered to elasmobranchs as a particularly effective repellent. Table 6 provides data establishing the repellent activity of naturally occurring aldehydes.

TABLE 6

|  | Hd-Syringe | | | Syringe | Cage | Total (Effective Delivery Methods) | | |
| --- | --- | --- | --- | --- | --- | --- | --- | --- |
| Compound | Y | R | N | Y | Y | Y | R | N |
| Cinnimaldehyde | | | | 2/2 | | 2/2 | | |
| Cuminaldehyde | | | | 1/1 | | 1/1 | | |
| Natural Aldehydes | 1/4 | 3/4 | | | | | 1/4 | 3/4 |
| Piperonal | | | | | 1/1 | 1/1 | | |
| Total | 1/4 | 3/4 | 3/3 | 1/1 | | 4/8 | 1/8 | 3/8 |
| Percent of Trials | 25% | 75% | 100% | 100 | | 50% | 13% | 38% |

"Y" denotes termination of tonic immobility.
"R" denotes a behavior response within tonic immobility.
"N" denotes no response.

The data in Table 6 evidences the repellent activity of naturally occurring aldehydes as elasmobranch repellents including cinnimaldehyde, cuminaldehyde and piperonal. In two of two Syringe assays for cinnimaldehyde on lemon and nurse sharks and one Syringe assay for cuminaldehyde on lemon shark, tonic immobility was terminated in each assay.

In an individual cage assay for piperonal, repellent activity was demonstrated by a decrease in the number of strikes by feeding sharks against a baited cage. In the piperonal assay, the sharks did not return to the baited cage after 10 minutes. In one of four Hd Syringe assays for natural aldehydes on nurse sharks, a behavioral change was observed within tonic immobility but tonic immobility was not terminated. In three of four Hd Syringe assays, no change was observed. The repellent activity evidenced in Table 6 should likewise apply to acetaldehyde. In view of the data in Table 6, effective compositions for repelling an elasmobranch comprising a natural aldehyde has been provided herein.

7. Aromatic Aldehydes

It is demonstrated herein that aromatic aldehydes such as a methoxy/vanillin combination, tolualdehyde, veratraldehyde, or anisaldehyde or any derivatives of any of the before-listed compounds may be administered to elasmobranchs as a particularly effective repellent. Table 7 provides data evidencing the repellent activity of aromatic aldehydes.

TABLE 7

| | Syringe | | |
|---|---|---|---|
| Compound | Y | R | N |
| Methoxy/Vanillin Combination | 6/9 | 2/9 | 1/9 |
| Tolualdehyde | 1/1 | | |
| Anisaldehyde | 1/1 | | |
| veratraldehyde | 6/7 | | 1/7 |
| Total | 14/18 | 2/18 | 1/18 |
| Percent of Trials | 78% | 11% | 6% |

"Y" denotes termination of tonic immobility.
"R" denotes a behavior response within tonic immobility.
"N" denotes no response.

Table 7 demonstrates the repellent effect of aromatic aldehyde on sharks. In six of nine Syringe Assays for methoxy/vanillin aldehyde mixture, tonic immobility was terminated among lemon, nurse and blacknose sharks. In two of nine, a behavioral change was observed in tonic immobility. In one of nine, no change was observed. In a single Syringe Assay for tolualdehyde and another for anisaldehyde, tonic immobility was terminated in lemons sharks. In six of seven Syringe Assays of veratraldehyde, tonic immobility in nurse and lemons sharks was observed. In one of seven Syringe Assays no response was noted. Such aldehydes may be administered into the vicinity of an elasmobranch in any method of delivery known in the art or herein disclosed. As such, effective compositions for repelling an elasmobranch comprising an aromatic aldehyde have been provided herein.

8. Longer Aldehydes and Combinations of Aldehydes

Aldehyde combinations or aldehydes having a chain length of 6 carbons or longer are effective elasmobranch repellents. It is demonstrated herein that aldehyde mixtures and aldehydes having a carbon chain of six carbons or longer or any derivatives thereof may be administered to elasmobranchs to repel them. Table 8 provides data evidencing the repellent activity of aldehydes with carbon chains longer than 6 carbons and combinations of aldehydes. Additional data evidencing the repellent activity of combinations of aldehydes may be seen in Table 23.

TABLE 8

| | Syringe | | | Bite | | | Syringe 3/5/10 | | |
|---|---|---|---|---|---|---|---|---|---|
| Compound | Y | R | N | Y | R | N | Y | R | N |
| octanal | 1/1 | | | | | | | | |
| nonanal | 1/1 | | | | | | | | |
| decanal | 1/1 | | | | | | | | |
| heptanal | | | 1/1 | | | | | | |
| mesityl oxide | 1/1 | | | | | | | | |
| octanal | 1/1 | | | | | | | | |
| Aldehyde Mixture BA1 | 7/7 | | | 6/6 | | | 2/2 | | |
| Total | 12/13 | | 1/13 | 6/6 | | | 2/2 | | |
| Percent of Trials | 92% | | 8% | 100% | | | 100% | | |

Eight-carbon octanal, nine-carbon nonanal, ten-carbon decanal and six-carbon mesityl oxide were tested on lemon sharks using a Syringe Assay. In each case, tonic immobility was terminated. In one Syringe Assay with heptanal, no response was observed. In seven of seven Syringe Assay tests for an aldehyde combination containing proprional, butanal, isobutanal, pentanal, hexanal, heptanal, octanal, nonanal, decanal, cuminal, cinnimal, anisal, mesityl oxide, p-tolualdehyde and veratraldehyde on lemon and blacktip sharks, tonic immobility was terminated. In two of two Syringe 3/5/10 Assay tests of the aldehyde combination on lemon and blacktip sharks, tonic immobility was terminated. In six of six Bite Assay tests of the aldehyde combination on nurse sharks, tonic immobility was terminated. In only a single Micropipette Assay test wherein 500 microliters of aldehyde mixture was delivered was no response observed.

Table 8 evidences the repellent effect of combinations of aldehydes and aldehydes having carbon chains 6 carbons or longer on a variety of sharks. Such aldehydes may be administered into the vicinity of an elasmobranch in any method of delivery known in the art or herein disclosed. As such, compositions for repelling an elasmobranch comprising aldehydes of lengths of six carbons and greater and combinations of aldehydes have been provided herein.

C. Composition for Repelling Elasmobranchs Comprising Carboxylic Acid

Carboxylic acids or derivatives thereof alone or in combinations are disclosed herein as effective elasmobranch repellents. Exemplary and non-limiting carboxylic acids include n-butyric acid, isobutyric acid, valeric acid, isovaleric acid, propanoic acid, citric acid, 2-butenoic acid (crotonic acid), 3-butenoic acid (cinylacetic acid), trans-cinnamic acid, 2-hydroxy-1,2,3-propanetricarboxylic acid, 1,2,3-propanetricarboxylic acid (tricarballylic acid), hydroxysuccinic acid (di-malic acid), 2,2-dimethylbutyric acid, 2,3,3-trimethylpropionic acid, 2,3-dimethylbutyric acid, 2-ethylbutyric acid, 2-ketobutyric acid, 2-methylisovaleric acid, 3-aminobutyric acid, and 4-acetylebutyric acid. Non-limiting exemplary carboxylic acids include dicarboxylic acids and tricarboxylic acids. Other naturally occurring acids that repel sharks include malic acid, lactic acid, succinic acid, fumaric acid and tricarballylic acid. These compounds may be used in powder (crystalline) form, or in aqueous or polar solvent solutions.

Carboxylic acids may be solubilized in any manner known to the art for administration into the expected environment of an elasmobranch. In a preferred composition, the carboxylic acid is prepared at a concentration of 0.1% w/w to 100% w/w in powder or liquid form wherein the powder is solubilized in water, ethanol or a suitable polar solvent. An exemplary mixture is 20% w/w 3-butenoic acid, 10% w/w citric acid, and 5% w/w/trancinnamic acid solubilized in 50:50 w/w water:ethanol.

Carboxylic acids disclosed herein include all carboxylic acids having the COOH function of a carboxylic acid. A preferred non-limiting class of carboxylic acids includes carboxylic acids comprising one to ten carbons. A more preferred non-limiting class of carboxylic acids comprises two to about five carbons. Another preferred non-limiting class of carboxylic acids comprises the dicarboxylic acids. Another preferred non-limiting class of carboxylic acids comprises the tricarboxylic acids.

The presence of butyric acid was detected in semiochemical extractions of decayed shark tissue using gas chromatography coupled with mass spectrometry and NIST structure libraries. Semiochemicals from decayed shark tissue have been shown to have properties that repel elasmobranchs. When n-butyric acid was presented to juvenile lemon or nurse sharks in tonic immobility, the immobility was terminated at mouth doses of 100 microliters.

Because n-butyric acid presents a very unpleasant odor during handling, its derivatives were studied. Screening of derivatives of butyric acid revealed the following compounds as repellents in lemon and nurse sharks. 2,2-Dimethylbutyric Acid, 2,3,3-Trimethylproprionic Acid, 2,3-Dimethylbutyric Acid, 2-Ethylbutyric Acid, 2-Ketobutyric Acid, 3-Aminobutyric Acid, 4-Acetylbutyric Acid. Also, compounds having the -enoic form of butyric acid were tested revealing the following shark repelling compounds: 2-butenoic acid and 3-butenoic acid. Additionally, naturally-occurring carboxylic acids were found to have shark repelling properties. Other carboxylic acids and carboxylic acid combinations were tested. Tables 9 and 10 provide a portion of the data of some carboxylic acids.

Table 9 demonstrates the repellent effect of butyric acid, butyric acid derivatives, enoic acid derivatives of butyric acid and naturally occurring carboxylic acids.

In a first Micropipette Assay on a juvenile lemon shark, an oral dose of no more than 100 microliters of butyric acid terminated tonic immobility. An oral dose of no more than 400 microliters was then delivered by micropipette into the mouth of a juvenile nurse shark. Tonic immobility was terminated. For each derivative of butyric acid and each naturally occurring acid listed in Table 9, a first micropipette assay was performed on a juvenile lemon shark with no more than 100 microliters of test acid in an oral dose. A second micropipette assay was then performed on a juvenile nurse shark with no more than 400 microliters of test acid in an oral dose. In each test, tonic immobility was terminated. This data evidences the gustatory repelling activity of carboxylic acids.

In four of four Hd Syringe assays, citric acid between 0.3 mL and 2.4 mL of citric acid 50% w/w was delivered about three inches from the mouth of a lemon shark. Each assay terminated tonic immobility. Seven Syringe 3/5/10 assays on nurse and lemons sharks were employed with crotonic acid solution. In four of the seven assays the crotonic acid was delivered directly to the mouth on a longline or within 10 inches of the shark's mouth. Tonic immobility was terminated. In one of the seven assays, the crotonic acid was delivered directly to the mouth of the shark on a longline and a behavioral response was observed in tonic immobility. In two of the seven assays, 6 mL of crotonic acid was delivered to lemon sharks at a distance of 36 inches from the shark's mouth. No response was observed. The lack of response is explained by the small volume delivered at a very large distance.

The data in Table 9 evidences the broad repellent activity of carboxylic acids and the exemplary and non-limiting repellent activity of butyric acid, butyric acid derivatives, enoic acids and naturally occurring carboxylic acids. Table 10 additionally evidences the repellent effect of lactic acid and carboxylic acid combinations.

TABLE 9

| Compound/Mixture | Hd-Syringe Y | Syringe 3/5/10 Y | Syringe 3/5/10 R | Syringe 3/5/10 N | Micropipette Y |
|---|---|---|---|---|---|
| n-Butyric Acid | | | | | 2/2 |
| 2,2-Dimethylbutyric Acid | | | | | 2/2 |
| 2,3,3-Trimethylproprionic Acid | | | | | 2/2 |
| 2,3-Dimethylbutyric Acid | | | | | 2/2 |
| 2-Ethylbutyric Acid | | | | | 2/2 |
| 2-Ketobutyric Acid | | | | | 2/2 |
| 2-Methylisovaleric Acid | | | | | 2/2 |
| 3-Aminobutyric Acid | | | | | 2/2 |
| 4-Acetylbutyric Acid | | | | | 2/2 |
| 3-Butenoic Acid (vinylacetic acid) | | | | | 2/2 |
| crotonic acid solution (2-butenoic acid) | | 4/7 | 1/7 | 2/7 | 2/2 |
| 4-acetylbutyric acid | | | | | 2/2 |
| trans-Cinnamic acid | | | | | 2/2 |
| Citric acid 50% w/w | 4/4 | | | | 2/2 |
| Tricarballylic Acid | | | | | 2/2 |
| Hydroxysuccinic Acid | | | | | 2/2 |
| Total | 4/4 | 4/7 | 1/7 | 2/7 | 30/30 |
| Percent of Trials | 100% | 71% | 14% | 29% | 100% |

"Y" denotes termination of tonic immobility.
"R" denotes a behavior response within tonic immobility.
"N" denotes no response.

TABLE 10

| Compound/Mixture | Syringe 3/5/10 Y | Syringe 3/5/10 R | Syringe 3/5/10 N | Cloud Dispersion Y |
|---|---|---|---|---|
| lactic acid | 2/3 | | 1/3 | |
| Crotonic/Cinnamic/Maleic Acid | 3/4 | 1/4 | | 1/1 |
| Crotonic/Citric/Fumaric Acid | 6/7 | 1/7 | | |
| Crotonic/Citric/Cinnamic | | | | 7/7 |
| Total | 15/21 | 3/21 | 1/27 | 8/8 |
| Percent of Trials | 71% | 14% | 19% | 100% |

"Y" denotes termination of tonic immobility.
"R" denotes a behavior response within tonic immobility.
"N" denotes no response.

In two of three Syringe 3/5/10 assays, lactic acid was delivered to lemon sharks and terminated tonic immobility. In a single Syringe 3/5/10 assay, lactic acid was delivered to a lemon shark and no behavioral change was observed. In three of four Syringe 3/5/10 assays, a mixture of Crotonic, Cinnamic and Maleic acids in glycol were delivered to tiger and blacknose sharks and terminated tonic immobility. In one of four Syringe 3/5/10 assays, delivery of the repellent actually missed the mouth of the shark and only a behavior change was seen in tonic immobility.

In a cloud dispersal assay of a mixture of Crotonic, Cinnamic and Maleic acids, 400 ml was dispersed from a diptube near the mouth of a great hammerhead shark. The shark fled the area and did not return.

In a surrounding cloud dispersal assay, 500 mL of a mixture of 20% w/w Crotonic acid, 10% w/w Citric acid and 5% w/w Cinnamic acid solubilized in 50:50 w/w water:ethanol was delivered in a subsurface dose in the vicinity of a population of competitively feeding sharks (5 Caribbean reef sharks and 2 blacknose sharks). The sharks were dispersed and did not return.

The data in Table 10 further evidences the broad repellent activity of carboxylic acids and mixtures of carboxylic acids. Together, Tables 9 and 10 evidence that carboxylic acids may be delivered into the vicinity of an elasmobranch in any method of delivery known in the art or herein disclosed to repel elasmobranchs. As such, a composition for repelling an elasmobranch comprising a carboxylic acid and derivatives thereof has been provided herein.

The composition for repelling an elasmobranch may comprise any carboxylic acid. It may preferably comprise a butyric acid, citric acid, a trans-cinnamic acid, 2-butenoic acid, lactic acid, 2,2-dimethylbutyric acid, 2,3,3-trimethylproprionic acid, 2-ethylbutyric acid, 2-detobutyric acid, 3-aminobutyric acid, 4-acetylbutyric acid, 3-butenoic acid, tricarballylic acid, hydroxysuccinic acid or any carboxylic acid that is deliverable to the environment of an elasmobranch, for example soluble in water or dissolved in a vehicle for delivery prior to delivery.

D. Composition for Repelling Elasmobranchs Comprising a Ketone or Di-Ketone

A composition for repelling an elasmobranch is provided herein comprising a ketone or a derivative thereof including, for example, ionone or zingerone, or a di-ketone or a derivative thereof, including, for example, 2,3-butanedione. Repelling characteristics of ketones and their derivatives and di-ketones and their derivatives are provided herein. Table 11 evidences the repellent activity of ketones and their derivatives and di-ketones and their derivatives.

Exemplary, non-limiting ketones and derivatives thereof include ionone, zingerone and derivatives thereof. Exemplary, non-limiting di-ketones and derivatives thereof include 2,3-butanedione, glyoxal and methylglyoxal. Data in Table 11 demonstrates the gustatory repellent activity of ketones and di-ketones.

In two individual cage assays for ionone and zingerone, repellent activity was demonstrated by a decrease in the number of strikes by feeding sharks against a baited cage. In both the ionone and zingerone assays, a decrease in the number of strikes at the cage was recorded when 500 mL of the repellent was delivered to the competitively feeding sharks. After a lull in feeding for 10 minutes, the sharks returned to the baited cage. See Example 5.

Tonic immobility studies were carried out on 2,3-butanedione and 2,3 butanedione (diacetyl) in denatured ethanol solution. In seven of eight Syringe Assays, tonic immobility was terminated in juvenile lemon and nurse sharks. In one Syringe Assay, a behavioral response was noted during tonic immobility. In one cloud dispersion assay in free-swimming Caribbean reef and blacknose sharks, no response was noted since the volume was only 290 microliters. No response would be expected with such a low volume. In one bite assay with a juvenile nurse shark, tonic immobility was terminated.

TABLE 11

| Compound | Syringe | | | Bite | | | Cloud/Cage | | |
|---|---|---|---|---|---|---|---|---|---|
|  | Y | R | N | Y | R | N | Y | R | N |
| Ionone |  |  |  |  |  |  | 1/1 |  |  |
| Zingerone |  |  |  |  |  |  | 1/1 |  |  |
| 2,3-butanedione | 7/8 |  | 1/8 | 1/1 |  |  |  |  | 1/1 |
| Total | 7/8 |  | 1/8 | 1/1 |  |  | 2/3 |  | 1/3 |
| Percent of Trials | 88% |  | 13% | 100% |  |  | 67% |  | 33% |

"Y" denotes termination of tonic immobility.
"R" denotes a behavior response within tonic immobility.
"N" denotes no response.

The data in Table 11 evidences the gustatory repellent activity of ketones, such as ionone and zingerone, and di-ketones, such as 2,3-butanedione. Other ketones having demonstrated gustatory repellent activity would include glyoxal and methylglyoxal.

E. Composition for Repelling Elasmobranchs Comprising a Pyridine

A composition for repelling an elasmobranch is provided herein comprising a pyridine or a derivative thereof including 2-methylpyridine (alpha-picoline, 3-methylpyridine (beta-picoline), 4-methylpyridine (gamma-picoline), lutidine (dimethylpyridine), and isomers of lutidine, collidine (trimethylpyridine) and isomers of collidine, 2-amino-3-picoline and derivatives of each or all of the pyridine derivatives. Repelling characteristics of pyridine and its derivatives are provided herein.

In initial investigations using tonic immobility assays in juvenile sharks, pyridine, alpha-picoline (2-methylpyridine), beta-picoline (3-methylpyridine), gamma-picoline (4-methylpyridine), lutidine and isomers thereof, collidine (trimethylpyridine) and isomers thereof and 3-amino-2-picoline all terminated tonic immobility when introduced to the mouth using a micropipette or syringe.

Table 12 provides some additional data demonstrating the repellent effect of pyridines and its derivatives in further investigations.

TABLE 12

| Compound | Hd-Syringe | | | Syringe 3/5/10 | | |
|---|---|---|---|---|---|---|
|  | Y | R | N | Y | R | N |
| Pyridine |  |  |  | 3/4 | 1/4 |  |
| 3-methylpyridine | 3/3 |  |  |  |  |  |
| Total | 3/3 |  |  | 3/4 | 1/4 |  |
| Percent Total | 100% | 0% | 0% | 75% | 25% | 0% |

"Y" denotes termination of tonic immobility.
"R" denotes a behavior response within tonic immobility.
"N" denotes no response.

In three of four Syringe 3/5/10 assays, pyridine was delivered to nurse and lemon sharks and terminated tonic immobility. In one of four Syringe 3/5/10 assays, delivery of pyridine evoke a change in behavior within tonic immobility of a nurse shark. In three of three Hd Syringe assays, delivery of 3-methylpyridine resulted in termination of tonic immobility. In two of two Micropipette assays on 2-amino-3-picoline 95% behavioral responses were noted in lemons sharks. In one, tonic immobility was terminated. In another, a violent seizure in the shark in response to the assay rendered measurement impossible.

Together the data in Table 12 demonstrate that pyridine and its derivatives such as 3-methylpyridine are good elasmobranch repellents. Pyridine is a simple heterocyclic aromatic organic compound that is structurally related to benzene, with one CH group in the six-membered ring replaced by a nitrogen atom. Pyridine has an equatorial lone pair of electrons at the nitrogen atom that does not participate in the aromatic pi-system. This makes pyridine a basic compound as well as a nucleophile. Pyridine is completely miscible in water.

The addition of one methyl group to the pyridine ring has no appreciable reduction on miscibility, particularly in seawater. Methylpyridines are commonly called "picolines." Methyl groups may occur at the α, β, γ positions relative to the nitrogen:

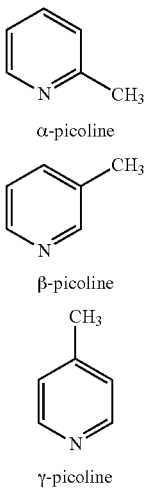

α-picoline

β-picoline

γ-picoline

It was not considered necessary to test all isomers because in a shark, isomers would not be expected to have steric effects that would alter the bioactivity of the compound since there are no electrophilic reactions occurring. As long as the compound is miscible or soluble in seawater, it is expected that it will find its way to a gustatory receptor site and activate it.

Two methyl functions on the pyridine ring have slight reduction on miscibility, particularly in seawater. Dimethylpyridines are commonly called "lutidines." Dimethylation may occur in the following positions:

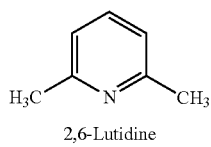

2,6-Lutidine

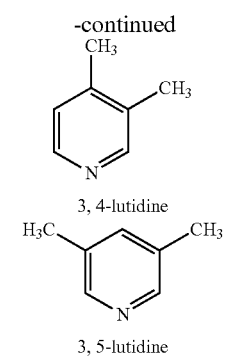

3,4-lutidine 3,5-lutidine

As discussed above, it was not considered necessary to test all isomers because in a shark, isomers would not be expected to have steric effects that would alter the bioactivity of the compound since there are no electrophilic reactions occurring.

Likewise, addition of three methyl functions to the pyridine ring has an appreciable reduction on miscibility, particularly in seawater. This compound is now only partially miscible, but is still bioactive. Trimethylpyridines are commonly called "collidines." Trimethyl functions may occur at the following positions:

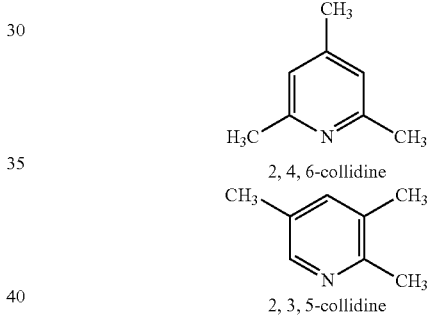

2, 4, 6-collidine 2, 3, 5-collidine

Toxicity is slightly reduced as methylation increases. Pyridine itself is not a preferred repellent because pyridine is a carcinogen and considered a marine pollutant. Likewise, picolines are less preferred repellents because they are irritants (making handling difficult) and are suspected carcinogens. While collidines may be the least irritative of all the methylpyridines, their toxicity decreases their preferability. Nevertheless, the repellent activity of these compounds is clearly disclosed herein.

It is reasonable to expect that alkyl, alkenyl, amino, hydroxyl, nitro, and halo-functions on the pyridine ring are useful gustatory repellents as well. For example, aminopicoline exhibited violent responses in juvenile sharks in the tonic immobility assay. Once again, however, the toxicity of this compound makes it less preferred from a handling, storage, and environmental standpoint.

F. Composition for Repelling Elasmobranchs Comprising an Anti-Pyrine

A composition for repelling an elasmobranch is provided herein comprising an anti-pyrine or a derivative thereof including anti-pyrine (phenazone) or 4-amino-antipyrine (metapirazone). Table 13 provides data evidencing the repellent activity of the anti-pyrines. In five of five Hd Syringe assays, 4-amino-antipyrine terminated tonic immobility in lemon and nurse sharks. Additionally, the data from two Micropipette assays demonstrate that antipyrine is a gustatory repellent. See Table 26.

TABLE 13

| | Hd-Syringe | | |
| Compound | Y | R | N |
|---|---|---|---|
| 4-amino-antipyrine (metapirazone) | 5/5 | | |
| Total Percent of Trials | 5/5 100% | | |

G. Composition for Repelling Elasmobranchs Comprising a Combination of Elasmobranch Repellents A composition for repelling an elasmobranch is provided herein comprising a combination of two or more of aldehydes or derivatives thereof, carboxylic acids or derivatives thereof, ketones or derivatives thereof, diketones or derivatives thereof, pyridines or derivatives thereof or antipyrines or derivatives thereof. It is expected that a combination of respective gustatory repellents will act together as a repellent composition. A composition may comprise a combination of any elasmobranch repellent.

For example, an effective elasmobranch repellent composition may comprise a number of aldehydes. See, e.g., Example 8, aldehyde repellent composition "BA1." A repellent composition may also, for example, comprise aldehydes and a di-ketone. A non-limiting preferred combination of aldehydes and a di-ketone may comprise butyraldehyde, isobutyraldehyde, veratraldehyde and 2,3-butanedione. See Example 8, aldehyde repellent composition "BA3." Likewise, a repellent composition may comprise, for example, a combination of crotonic acid, citric acid and fumaric acid, or a combination of crotonic acid, cinnamic acid and maleic acid. See Table 24. Each of these combinations, along with a variety of other combinations disclosed herein, evidence repellent characteristics. See, e.g., Tables 23-24.

The data in Examples 8 and 9 and Tables 23 and 24, together with the disclosure provided herein, evidence the effectiveness of combinations of elasmobranch repellents as elasmobranch repellent compositions.

H. A Method of Manufacturing an Elasmobranch Repellent

The repellents and methods describe herein provide the artisan with chemicals that have been demonstrated to repel, at very low concentrations, families of shark known to migrate in shallow coastal waters and species known to attack humans. As such, one of skill in the art will recognize from the breadth of repellents disclosed herein that an elasmobranch repellent may be manufactured by combining an aldehyde or a derivative thereof, a carboxylic acid or a derivative thereof, a ketone or a derivative thereof, a di-ketone or a derivative thereof, a pyridine or a derivative thereof, or an antipyrine or a derivative thereof, separately or in combination, with an acceptable solvent, carrier, diluent or other vehicle for administration or storage. An exemplary solvent is ethanol or ethanol:water (50:50 w/w). Ethanol and water are excellent solvents for elasmobranch repellents because they are not prohibited by federal regulations from dispersion in sea water. Other exemplary solvents include acetonitrile, dimethyl sulfoxide (DMSO), denatured alcohol, C3-C4 glycols (2,3-propanediol, butanediol), glycol ethers (diethylene glycol monoethyl ether), and glycol ether esters.

An elasmobranch repellent may also be manufactured by crystallizing any of the above-discussed compounds and preparing them as a powder to be dispensed into water. Powdered substances may be combined with carriers to improve solubility or handling. One skilled in the art would recognize many different carriers or diluents that may be combined with a powder of any of the repellents discussed herein.

III. METHODS AND DEVICES OF DELIVERY OF REPELLENT

A. Method for Repelling Elasmobranch with Gustatory Compounds

Also provided herein is a method of repelling an elasmobranch comprising administering a composition for repelling an elasmobranch comprising an aldehyde or a derivative thereof, a carboxylic acid or a derivative thereof, a ketone or a derivative thereof, a di-ketone or a derivative thereof, a pyridine or a derivative thereof, or an antipyrine or a derivative thereof, separately or in combination, in the expected proximity of said elasmobranch.

Any of the repellents disclosed herein may be delivered to the environment of an elasmobranch through a variety of methods and devices of delivery. These compounds are most useful when they can be directed into a shark's mouth or into the environment where the repellent may enter the shark's mouth. As such, a squirt gun or long syringe is a good delivery vehicle. The repellents disclosed herein may likewise be incorporated into lotions, longline time-release gels, time-release sponges, jelly's or any other delivery device or substance contemplated by one of skill in the art.

An extensive disclosure of devices for delivery of chemical repellents into the vicinity of an elasmobranch is provided in PCT/US06/05035. Delivery devices disclosed therein include, e.g., pressurized delivery pole apparatuses, syringes, cattle-treatment "drench" guns, aerosol canisters, mortar-launched aerosol "bomb" canisters, automated repellent dispensers on a raft or fixed to some other object, repellent dischargers, pouches containing repellents, apparatuses for administering repellent along fishing longline, repellent backpack dischargers for use, for example, by scuba divers and those who snorkel, spear guns fitted with a repellent discharge device, delivery devices for surfboards, wristwatches, belts and bracelets. Each of the devices and suggestions for devices disclosed therein may be applied to delivery of the compounds disclosed herein. PCT/US06/05035, filed Feb. 13, 2006, is incorporated in its entirety herein by reference.

Most aldehydes will oxidize in air. Therefore, it is prudent to stabilize the aldehyde when it is stored, especially in the warm climates. In a non-limiting preferred handling method, the practitioner may use a pinch of hydroquinone or sodium iodide with 3-methylbutanal or other aldehyde. The mixture may be stored under nitrogen. This method keeps the aldehyde fresh and effective. If an aldehyde oxidizes (in the case of 3-methylbutanal to becomes isovaleric acid, which smells like feet or cheese) the resulting acid may be less potent than the aldehyde.

Many of the gustation compounds disclosed herein are regulated under federal environmental regulations. Some are considered marine pollutants, and others, like pyridine and aminopyridine are considered toxic. However, some, such as 3-methylbutanal, 2-methylbutanal, 3-methylbutenal, 2-methylbutenal, trans-pentenal, piperonal, etc., are very safe and meet federal regulations.

B. Delivery Devices for Gustatory Compounds

Alternative methods for delivering a chemical repellent into an elasmobranch environment include a miniature pressurized repellent gun to be worn on the wrist or ankle, a spear fishing gun with an adjacent repellent cylinder, a time release sponge-material attached to a surfboard or otherwise placed near a diver, swimmer or in some other place of interest, a hollow surfboard with a calibrated drip to emit repellent, a pump delivery system affixed to a surfboard, a pressurized delivery device affixed to a surfboard wherein discharge of repellent may be triggered by the surfer, a floatation device, a wristwatch filled with repellent (pressurized or unpressurized), a carbon dioxide activated pressurized syringe, an aerosol bomb, a mortar-launched aerosol bomb, a remote-controlled buoy with a repellent tank that may be fired by a lifeguard or other person or mechanized system, a buoy with a metering pump that runs during swim time (daylight), a repellent pouch attached to longlines (muslin/burlap bags) or to clothing or surfboard or other water device, jellied repellent (glycol ether/hydroxypropylcelluose gels which time-dissolve in water), sunscreen/sun care formulations containing repellent, lotions containing repellent, porous fabric impregnated with repellent, rechargeable porous fabric impregnated with repellent, a kite- or balloon-deployed repellent bomb (remote control), a submerged repellent mine (remote control) for deeper water, a cattle-treatment drench gun converted to shark repellent gun (http://www.dr-register.com/drenchgun.htm), repellent-impregnated cable insulation and cable jackets for undersea lines.

Chemical repellents disclosed herein may be discharged through a pressurized tube that runs alongside an extended or extendable poll. The pressurized delivery pole apparatus may be useful for administering repellent to feeding or otherwise stimulated sharks. The apparatus may comprise a delivery device housing (pole) with a repellent discharge tube housed along or within the pole. The repellent discharge tube may be connected to a pressurized chamber or chambers containing repellent. The delivery device may contain a check valve to facilitate the maintenance of pressure. A trigger may allow the pressurized repellent to discharge through the tube and away from the pole. An alternative delivery device may be a pressurized syringe. Such a syringe may be filled with repellent.

1. Pressurized Container Delivery Device

An alternative delivery method may be a pressurized container of repellent such as an aerosol canister. The container may be constructed of degradable material. The aerosol canister may have sufficient pressure and repellent to be discharged in the water and repel sharks in the area. The container may be asymmetrically weighted to provide an erratic movement in the water as it discharges repellent. The aerosol container may further comprise an actuator that when engaged allows the compressed contents of the aerosol container to be expelled. The device further preferably comprises a continuous discharge apparatus to allow the contents of the can to be expelled with a single activation of the discharge apparatus. Preferably, when the actuator is engaged, the nozzle remains open to allow the can to be continuously and fully evacuated. The actuator may be made of a soluble material that allows discharge when exposed to water.

2. Raft/Buoy Delivery Device

Another delivery device is a raft or other floating or fixed device comprising a floating buoy, a solid platform, and a container of repellent connected to a pump with a power source that is capable of delivering repellent into a shark environment either by automatic timing, remote triggering or other actuating mechanism. The container comprises a check valve that allows the pump to build pressure in the container to a desired pressure. When a desired pressure is achieved, a release valve or pressure-release cap releases the pressurized repellent into a delivery tube. The repellent is expelled across the water, spreading a wide cloud of repellent.

The pump may be automatically activated by a timer or may be activated remotely. The pump preferably delivers sufficient repellent into the water to repel sharks. Preferably, the discharge tube is long enough and not submerged such that when delivery begins, the repellent is sprayed a substantial distance onto the surface of the water and, under pressure, the discharge tube moves erratically across a large radial area in relation to the raft. In a preferred method the discharge tube is made of flexible material. Preferably the discharge tube will spray over an entire 360 degree arc.

3. Pouch

Another delivery device is a pouch containing repellent or a sponge treated with repellent. Repellent may be in the form of a solution or solid, preferably partly or wholly soluble. The repellent may be introduced to the environment of the shark by diffusion or by rupturing, tearing or otherwise penetrating the pouch. A pouch may also diffuse repellent through its fabric. A diffusing pouch may be attached to a fishing net or longline with a baited hook on a snood to allow repellent to slowly diffuse into the water surrounding bate or fishing net. The pouch will provide sufficient repellent around the baited hook to repel sharks while not repelling the desired teliost fish. A pouch to be placed on a longline may preferably be constructed of muslin or burlap.

4. Longline Apparatus

Sharks represent a significant problem in the long line fishing industry. Chemical repellents on longlines in accordance with the invention are preferably soluble in seawater, and, at a sufficient concentration to produce flight responses in elasmobranches. Teleost fish are not affected by the chemical repellents.

Another delivery device is an apparatus for administering repellent along longline fishing tackle. The apparatus comprises a pressurized chamber connected to a source of compressed gas, contains repellent and is connected to a primary delivery tube. The primary delivery tube is positioned adjacent to or otherwise in concert with the longline. Additional secondary delivery tubes are joined to the primary delivery tube in proximity to each snood of the longline. The secondary delivery tubes terminate near the baited hook of the snood. When pressurized repellent is released from the chamber, the repellent is delivered along the primary delivery tube and into the secondary delivery tubes thereby discharging repellent near the baited hook and repelling sharks from the bait.

C. Kit for Repelling Elasmobranch

The skilled artisan will recognize from the disclosure herein that a kit may be compiled comprising a composition for repelling an elasmobranch comprising an aldehyde or a derivative thereof, a carboxylic acid or a derivative thereof, a ketone or a derivative thereof, a di-ketone or derivative thereof, a pyridine or a derivative thereof, or an antipyrine or a derivative thereof and a vehicle of administering said repellent.

In a preferred combination for a kit, the vehicle is selected from the group consisting of a pressurized or pressurizable delivery device, a pressurized or pressurizable repellent gun, a miniature pressurizable repellent gun to be warn on a wrist or an ankle of a subject, a spear fishing gun with an adjacent pressurizable repellent container, a time release sponge, a surfboard, a pump delivery system affixed to a surfboard, a pressurized delivery device affixed to a surfboard, a wristwatch comprising said repellent, a syringe, a pressurized syringe, an aerosol bomb, a mortar-launched aerosol bomb, a remote-controlled buoy with a repellent tank, a fixed buoy with a metering pump, a repellent pouch, a jelly comprising glycol ether and hydroxypropylcelluose, a skin lotion containing said repellent, a porous fabric impregnated with repellent, rechargeable porous fabric impregnated with said repellent, a submerged repellent mine, a repellent-impregnated cable insulation for an undersea cable, and a repellent-impregnated cable jacket for an undersea cable.

The invention is further described with the following non-limiting examples, which are provided to further illuminate aspects of the invention.

IV. EXAMPLES

Example 1

Methylbutanal Elasmobranch Repellents

Tonic immobility studies were carried out on lemon, nurse, tiger and blacktip sharks with 3-methylbutanal and 2-methylbutanal using Hd Syringe, Syringe 3/5/10 and Bite assays. In 40 of 41 total assays for repellent effect, tonic immobility was terminated or the sharks demonstrated a change of behavior during tonic immobility upon delivery of 3-methylbutanal. In Micropipette assays, a gustatory response to the deliver of 3-methylbutanal was observed in 16 of 20 assays.

Lemon, nurse, blacktip and tiger sharks were placed in tonic immobility by inverting the shark's body along its longitudinal axis. Each shark was observed to enter a tonic state of paralysis. The "tonic" state of each shark was first established by releasing a control of seawater in proximity to the shark with the same delivery instrument and at the same distance as the chemical repellent would later be delivered. In certain controls, sea water was released with a high flow rate (30 mL/sec) in order to establish that the sharks would not be awakened by a jet of fluid over their noses.

Once behavioral controls were established, the chemical repellent was delivered to the shark using the Hd Syringe Assay method, the Syringe 3/5/10 Assay method, the Bite Assay method or the Micropipette Assay method. The shark was observed for any behavioral response. If tonic immobility was terminated, the positive response was denoted as "Y." If tonic immobility was not terminated but a behavior change within tonic immobility was noted, such as the opening of the mouth or a cough, the response was denoted as an "R" for reduced response. If no behavior change was observed, the negative response was denoted "N."

In Hd-Syringe Assays, the 3-methylbutanal was delivered to the shark's mouth and nares using a 3 mL hypodermic syringe fitted with a 22 gauge needle. The needle was held within 3 inches of the shark's mouth and the test repellent was slowly released from the syringe with a very fine plume in the water column. Any response was denoted. If a response occurred during a measurable time after delivery of the test chemical, the time between delivery and response was noted. If a response occurred immediately or the response occurred before a measurable time could be established, no time to response was noted.

Because the test chemical repellent is delivered at a distance from the shark's nares and mouth, a cloud of test chemical repellent is dispersed over the shark within the water column. The dispersed test repellent is subject to water current direction, dispersion and dilution. As a result, the time between delivery of the chemical repellent and a response was not correlatable with volume of delivered repellent or potency of repellent. Instead, the time between delivery and response was usually related to water current.

In Syringe 3/5/10 Assays, 5-6 mL of 3-methylbutanal was delivered at least 3 inches in front of the shark's mouth. A cloud of the repellent dispersed over the shark within the water column. The shark was observed for a behavioral response. A behavioral response within 10 seconds was considered a positive flight response. Time from delivery of the repellent until behavioral response was recorded, if measurable. As noted above, because the dispersion of the chemical repellent upon delivery is affected by volume of repellent, water current, and other factors, the time between delivery and response was not correlatable with the potency of the repellent.

In Bite Assays, a dose of typically less than 5 mL of 3-methylbutanal was presented directly into the shark's mouth using a pipette. The shark was observed for behavioral response as above. Because the delivery was directly into the shark's mouth and responses were generally observed immediately upon delivery, time to response was not recorded.

Twenty seven Hd Syringe Assays were performed. Eleven assays on juvenile lemon sharks, 15 assays on juvenile nurse sharks and one assay on a tiger shark. See Table 14. In 74% of assays tonic immobility was terminated indicated a flight response. In 22% of assays a behavioral change was observed indicating a response to the chemical repellent. In one assay no response was observed. See Table 14.

Seven Syringe 3/5/10 Assays were performed. One assay on a juvenile lemon shark, two assays on juvenile nurse sharks, three assays on blacktip sharks and one assay on a tiger shark. 100% of assays terminated tonic immobility indicating a flight response. Two Bite assays were performed on nurse sharks each resulting in termination of tonic immobility indicating a flight response. In total, 97% of assays resulted in a positive response to 3-methylbutanal and 81% resulted in direct termination of tonic immobility demonstrating a strong repelling effect for 3-methylbutanal. See Table 14.

Twenty Micropipette Assays were performed on juvenile lemon sharks and juvenile nurse sharks. In fifteen assays a gustatory response was observed (five terminated tonic immobility, ten behavioral responses observed). In five assays no response was observed. These data demonstrate the gustatory repellent activity of 3-methylbutanal because the repellent is delivered directly into the mouth of the shark and no repellent is available to the nose of the shark. See Table 14.

Because Micropipette assays deliver very small volumes into the mouth of the shark, the volume of repellent is at times not sufficient to evoke termination of tonic immobility and, more rarely, is not sufficient to evoke a response. Further because the Micropipette assays were often done serially on the same set of sharks, second and third doses of the repellent over time would be expected to evoke less of a reaction. Nevertheless, the small doses delivered to the shark in the Micropipette assay provide important data on whether a compound is a gustatory stimulant because the small dose may be delivered directly into the mouth of the shark. This eliminates any olfactory response that might be acting in concert with a gustatory response to terminate tonic immobility.

In each assay disclosed herein, a control of sea water was performed prior to the testing of each test repellent. In the control, sea water was delivered to the shark to be tested in the same delivery manner as the test repellent was delivered. If the shark made no response to the delivery of sea water, the control was considered successful. Subsequently, the test repellent was delivered to the shark. In Cloud Dispersion assays and Cage assays, sea water or dye control was delivered to the test shark population prior to delivery of repellent.

Controls were performed in each assay reported herein and yielded no response from the subject shark. Control data is not illustrated in the data tables provided in this example or throughout. Nevertheless, each data point was subject to a control prior to the testing of each compound.

TABLE 14

Tonic Immobility Assays with 3-Methylbutanal

| Component | Species | TTI | Delivery | Dose | Response |
|---|---|---|---|---|---|
| 3-methylbutanal | Lemon | R | Hd syringe | 3.6 ml | |
| 3-methylbutanal | Lemon | R | Hd syringe | 1.4 ml | |
| 3-methylbutanal | Lemon | Y | Hd syringe | 400 ul | |
| 3-methylbutanal | Lemon | Y | Hd syringe | 500 ul | |
| 3-methylbutanal | Lemon | Y | Hd syringe | 0.6 ml | 6.27 sec |
| 3-methylbutanal | Lemon | Y | Hd syringe | 0.3 ml | 2.73 sec |
| 3-methylbutanal | Lemon | Y | Hd syringe | 0.3 ml | 2.17 sec |
| 3-methylbutanal | Lemon | Y | Hd syringe | 0.5 ml | 4.53 sec |
| 3-methylbutanal | Lemon | R | Hd syringe | 1 ml | 1.7 sec |
| 3-methylbutanal | Lemon | Y | Hd syringe | 1.6 ml | 9.52 sec |
| 3-methylbutanal | Lemon | N | Hd syringe | 1.4 ml | |
| 3-methylbutanal | Nurse | Y | Hd syringe | 0.6 ml | |
| 3-methylbutanal | Nurse | R | Hd syringe | 0.8 ml | |
| 3-methylbutanal | Nurse | Y | Hd syringe | 1.6 ml | |
| 3-methylbutanal | Nurse | Y | Hd syringe | 400 ul | |
| 3-methylbutanal | Nurse | Y | Hd syringe | 150 ul | |
| 3-methylbutanal | Nurse | Y | Hd syringe | 350 ul | |
| 3-methylbutanal | Nurse | R | Hd syringe | 0.4 ml | 1.28 sec |
| 3-methylbutanal | Nurse | R | Hd syringe | 0.8 ml | 2.80 sec |
| 3-methylbutanal | Nurse | Y | Hd syringe | 1.2 ml | 4.39 sec |
| 3-methylbutanal | Nurse | Y | Hd syringe | 0.2 ml | 0.64 sec |
| 3-methylbutanal | Nurse | Y | Hd syringe | 0.2 ml | 0.89 sec |
| 3-methylbutanal | Nurse | Y | Hd syringe | 0.2 ml | 0.76 sec |
| 3-methylbutanal | Nurse | Y | Hd syringe | 0.15 ml | 1.08 sec |
| 3-methylbutanal | Nurse | Y | Hd syringe | 0.1 ml | 0.82 sec |
| 3-methylbutanal | Nurse | Y | Hd syringe | 0.2 ml | 1.00 sec |
| 3-methylbutanal | Tiger | Y | Hd syringe | 1 ml | 1 sec |
| 3-methylbutanal | Lemon | Y | syringe 3/5/10 | 6 ml | 2 sec |
| 3-methylbutanal | Nurse | Y | syringe 3/5/10 | 3 ml | 2 sec |
| 3-methylbutanal | Nurse | Y | syringe 3/5/10 | 3 ml | 2 sec |
| 3-methylbutanal | Blacktip | Y | syringe 3/5/10 | 6 ml | 5 sec |
| 3-methylbutanal | Blacktip | Y | syringe 3/5/10 | 6 ml | 2.75 sec |
| 3-methylbutanal | Blacktip | Y | syringe 3/5/10 | 6 ml | 1.47 sec |
| 3-methylbutanal | Tiger | Y | syringe 3/5/10 | 6 ml | 3.46 sec |
| 3-methylbutanal | Nurse | Y | bite | 3.6 ml | |
| 3-methylbutanal | Nurse | Y | bite | 2 ml | |
| 3-methylbutanal | Lemon | Y | micropipette | 150 ul | |
| 3-methylbutanal | Lemon | R | micropipette | 150 ul | |
| 3-methylbutanal | Lemon | R | micropipette | 150 ul | |
| 3-methylbutanal | Lemon | R | micropipette | 200 ul | |
| 3-methylbutanal | Lemon | R | micropipette | 250 ul | |
| 3-methylbutanal | Lemon | Y | micropipette | 400 ul | |
| 3-methylbutanal | Lemon | R | micropipette | 400 ul | |
| 3-methylbutanal | Lemon | R | micropipette | 400 ul | |
| 3-methylbutanal | Lemon | N | micropipette | 250 ul | |
| 3-methylbutanal | Lemon | N | micropipette | 250 ul | |
| 3-methylbutanal | Lemon | N | micropipette | 200 ul | |
| 3-methylbutanal | Lemon | Y | micropipette | 200 ul | |
| 3-methylbutanal | Lemon | N | micropipette | 100 ul | |
| 3-methylbutanal | Lemon | R | micropipette | 150 ul | |
| 3-methylbutanal | Lemon | R | micropipette | 200 ul | |

TABLE 14-continued

Tonic Immobility Assays with 3-Methylbutanal

| Component | Species | TTI | Delivery | Dose | Response |
|---|---|---|---|---|---|
| 3-methylbutanal | Nurse | R | micropipette | 400 ul | |
| 3-methylbutanal | Nurse | Y | micropipette | 400 ul | |
| 3-methylbutanal | Nurse | Y | micropipette | 400 ul | |
| 3-methylbutanal | Nurse | R | micropipette | 270 ul | |
| 3-methylbutanal | Nurse | R | micropipette | 270 ul | |

Five Hd Syringe assays were performed on juvenile lemon and nurse sharks using 2-methylbutanal. In each assay tonic immobility was terminated demonstrating a flight response and the repellent activity of 2-methylbutanal. See Table 15.

TABLE 15

Tonic Immobility Assays with 2-Methylbutanal

| Component | Species | T? | Delivery | Dose |
|---|---|---|---|---|
| 2-methylbutanal | Lemon | Y | hd syringe | 400 ul |
| 2-methylbutanal | Lemon | Y | hd syringe | 200 ul |
| 2-methylbutanal | Nurse | Y | hd syringe | 500 ul |
| 2-methylbutanal | Nurse | Y | hd syringe | 200 ul |
| 2-methylbutanal | Nurse | Y | hd syringe | 200 ul |

Example 2

Methylbutenal Elasmobranch Repellents

Tonic immobility studies were carried out on lemon and nurse sharks with 3-methylbutenal and 2-methylbutenal using Hd Syringe and Micropipette assays as described above in Example 1. One Hd Syringe assay was performed on a juvenile lemon shark using 2-methylbutenal. Three Hd Syringe assays were likewise performed on juvenile nurse sharks. All assays resulted in termination of tonic immobility demonstrating the repellent activity of 2-methylbutenal. See Table 16.

TABLE 16

Tonic Immobility Assays with 2-Methylbutenal

| Component | Species | T? | Delivery | Dose |
|---|---|---|---|---|
| 2-methylbutenal | Lemon | Y | hd syringe | 300 ul |
| 2-methylbutenal | Nurse | Y | hd syringe | 450 ul |
| 2-methylbutenal | Nurse | Y | hd syringe | 400 ul |
| 2-methylbutenal | Nurse | Y | hd syringe | 1700 ul |

Hd Syringe assays were likewise performed using 3-methylbutenal. One assay was performed on a juvenile lemon shark. Three assays were performed on juvenile nurse sharks. All assays resulted in termination of tonic immobility demonstrating the repellent activity of 3-methylbutenal. See Table 17.

TABLE 17

Tonic Immobility Assays with 3-Methylbutenal

| Component | Species | T? | Delivery | Dose |
|---|---|---|---|---|
| 3-methylbutenal | Lemon | Y | hd syringe | 350 ul |
| 3-methylbutenal | Nurse | Y | hd syringe | 700 ul |

TABLE 17-continued

Tonic Immobility Assays with 3-Methylbutenal

| Component | Species | T? | Delivery | Dose |
|---|---|---|---|---|
| 3-methylbutenal | Nurse | Y | hd syringe | 100 ul |
| 3-methylbutenal | Nurse | Y | hd syringe | 1000 ul |
| 3-methylbutenal | Lemon | R | micropipette | 400 ul |
| 3-methylbutenal | Lemon | R | micropipette | 400 ul |
| 3-methylbutenal | Lemon | Y | micropipette | 400 ul |
| 3-methylbutenal | Nurse | R | micropipette | 400 ul |
| 3-methylbutenal | Nurse | R | micropipette | 400 ul |
| 3-methylbutenal | Nurse | R | micropipette | 400 ul |

As evidenced in Tables 16 and 17, methylbutenal is an effective elasmobranch repellent because tonic immobility was terminated in all test species when an HD Syringe Assay was employed and a gustatory response was observed in all Micropipette Assays. See Tables 16 and 17.

Example 3-5

Carbon Aldehyde Elasmobranch Repellents

Tonic immobility studies were carried out on juvenile lemon and nurse sharks using the linear 5-carbon aldehydes, valeraldehyde and trans-pentenal with Hd Syringe and Micropipette assays as described above in Example 1. One Syringe assay was carried out on a juvenile nurse shark.

In the Syringe assay about 60 mL or more of valeraldehyde was delivered from one to as many as five feet from the shark depending on the water current. Time from delivery of the test substance until a response was observed, measured and recorded. Time from delivery to response was related to the size of the bolus delivered from the syringe, distance of the shark from the syringe and water current. As such, a longer time to response does not reflect reduced potency for a particular compound. To the contrary, a longer time to response as compared to some other compound or test simply demonstrates that even after a cloud of repellent has traveled some distance against water current, the potency of the repellent is demonstrated.

Two Hd Syringe assays were performed on juvenile lemon sharks with valeraldehyde. Likewise, three Hd Syringe assays were performed on juvenile nurse sharks and one Syringe assay was performed on a juvenile nurse shark. In all assays valeraldehyde terminated tonic immobility demonstrating the repellent activity of valeraldehyde. In six of six Micropipette assays (three on lemon sharks and three on nurse sharks) a change in behavior during tonic immobility was observed. This demonstrates the gustatory activity of valeraldehyde. See Table 18.

Two Hd Syringe assays were performed on lemon sharks with trans-pentenal and three Hd Syringe assays were likewise performed on nurse sharks. In all assays tonic immobility was terminated demonstrating the repellent activity of valeraldehyde. In six of six Micropipette assays (three on lemon sharks and three on nurse sharks) a change in behavior during tonic immobility was observed. In five of the Micropipette assays tonic immobility was terminated. This strongly evidences the gustatory activity of trans-pentenal. See Table 18.

TABLE 18

Tonic Immobility Assays with Valeraldehyde and Trans-Pentenal

| Component | Species | T? | Delivery | Dose | Response |
|---|---|---|---|---|---|
| valeraldehyde | Lemon | Y | hd syringe | 350 ul | |
| valeraldehyde | Lemon | Y | hd syringe | 250 ul | |
| valeraldehyde | Nurse | Y | hd syringe | 400 ul | |
| valeraldehyde | Nurse | Y | hd syringe | 100 ul | |
| valeraldehyde | Nurse | Y | hd syringe | 300 ul | |
| valeraldehyde | Nurse | Y | syringe | 52 ml | 15.5 sec |
| valeraldehyde | Lemon | R | micropipette | 400 ul | |
| valeraldehyde | Lemon | R | micropipette | 400 ul | |
| valeraldehyde | Lemon | R | micropipette | 400 ul | |
| valeraldehyde | Nurse | R | micropipette | 400 ul | |
| valeraldehyde | Nurse | R | micropipette | 400 ul | |
| valeraldehyde | Nurse | R | micropipette | 400 ul | |
| trans-pentenal | Lemon | Y | hd syringe | 300 ul | |
| trans-pentenal | Lemon | Y | hd syringe | 250 ul | |
| trans-pentenal | Nurse | Y | hd syringe | 150 ul | |
| trans-pentenal | Nurse | Y | hd syringe | 300 ul | |
| trans-pentenal | Nurse | Y | hd syringe | 400 ul | |
| trans-pentenal | Lemon | Y | micropipette | 400 ul | |
| trans-pentenal | Lemon | Y | Micropipette | 400 ul | |
| trans-pentenal | Lemon | R | Micropipette | 400 ul | |
| trans-pentenal | Nurse | R | Micropipette | 400 ul | |
| trans-pentenal | Nurse | Y | Micropipette | 400 ul | |
| trans-pentenal | Nurse | Y | Micropipette | 400 ul | |

As evidenced in Table 18, linear 5-carbon aldehydes, valeraldehyde and trans-pentenal, were observed to be effective elasmobranch repellents in two different species using three different assays. In combination with the data provided in Tables 14-17, the data herein evidences that linear 5-carbon aldehydes are effective elasmobranch repellents.

Example 4

Saturated C1-C6 Aldehyde Elasmobranch Repellents

Tonic immobility studies were carried out on juvenile lemon and nurse sharks using aldehydes with saturated carbon chains comprising 3 carbons to about 6 carbons including propionaldehyde, butyraldehyde, isobutyraldehyde, valeraldehyde, capronaldehyde, trimethylacetaldehyde. In combination with the study of 3-methylbutanal and 2-methylbutanal in Example 1 and the study of valeraldehyde and trans-pentenal in Example 3, the data provided herein evidences the repellent activity of aldehydes with saturated carbon chains comprising 3 carbons to about 6 carbons. These data may also be applied to the one and two carbon-chain compounds formalin and acetaldehyde because they are highly water soluble and are expected to exhibit the same bio-activity on gustatory receptors as the longer aldehydes.

Syringe, Hd Syringe, Syringe 3/5/10 and Micropipette assays were carried out as described in Examples 1 and 2.

Using propionaldehyde, a three carbon aldehyde, four Syringe assays were performed. Two on nurse sharks and two on lemon sharks. All resulted in termination of tonic immobility thereby demonstrating the repellent activity of propionaldehyde. See Table 19.

Using butyraldehyde, a four carbon aldehyde, two Syringe assays were performed on lemon sharks resulting in termination of tonic immobility; three Syringe assays were performed on nurse sharks, two resulted in termination of tonic immobility and one had no result. Because 4 of 5 assays resulted in termination of tonic immobility, the repellent activity of butyraldehyde was demonstrated. See Table 19.

Using isobutyraldehyde, another four carbon aldehyde, three Syringe assays were performed on lemon sharks and one Syringe assay was performed on a nurse shark. All resulted in termination of tonic immobility demonstrating the repellent activity of isobutyraldehyde. See Table 19.

Using trimethylacetaldehyde, a five carbon aldehyde, three Hd Syringe assays on juvenile nurse sharks, two Hd Syringe assays on juvenile lemon sharks and two Syringe 3/5/10 assays on juvenile nurse sharks resulted in termination of tonic immobility. The data clearly demonstrate the repellent activity of trimethylacetaldehyde. See Table 19.

Micropipette assays using trimethylacetaldehyde resulted in a change of behavior during tonic immobility in three juvenile nurse sharks and three juvenile lemon sharks. These data demonstrate the gustatory effect of trimethylacetaldehyde. See Table 19.

TABLE 19

Tonic Immobility Assays with Saturated C1-C6 Aldehydes

| Component | Species | T? | Delivery | Dose | Response |
|---|---|---|---|---|---|
| propionaldehyde | nurse | Y | syringe | 35 ml | 7.79 sec |
| propionaldehyde | nurse | Y | syringe | 20 ml | 4.99 sec |
| propionaldehyde | lemon | Y | syringe | 18 ml | 2.87 sec |
| propionaldehyde | lemon | Y | syringe | 37 ml | 8.53 sec |
| butyraldehyde | lemon | Y | syringe | 23 ml | 4.75 sec |
| butyraldehyde | lemon | Y | syringe | 23 ml | 5.66 sec |
| butyraldehyde | nurse | Y | syringe | 21 ml | 3.23 sec |
| butyraldehyde | nurse | N | syringe | 33 ml | |
| butyraldehyde | nurse | Y | syringe | 23 ml | 4.75 sec |
| isobutyraldehyde | lemon | Y | syringe | 4 ml | 1.30 sec |
| isobutyraldehyde | lemon | Y | syringe | 9 ml | 2.61 sec |
| isobutyraldehyde | lemon | Y | syringe | 6 ml | 1.28 sec |
| isobutyraldehyde | nurse | Y | syringe | 60 ml | 11.92 sec |
| capronaldehyde | lemon | Y | syringe | 27 ml | 3.21 sec |
| trimethyl-acetaldehyde | Nurse | Y | Hd syringe | 200 ul | |
| trimethyl-acetaldehyde | Nurse | Y | Hd syringe | 100 ul | |
| trimethyl-acetaldehyde | Nurse | Y | Hd syringe | 300 ul | |
| trimethyl-acetaldehyde | Lemon | Y | Hd syringe | 600 ul | |
| trimethyl-acetaldehyde | Lemon | Y | Hd syringe | 200 ul | |
| trimethyl-acetaldehyde | nurse | N | syringe 3/5/10 | 4 ml | |
| trimethyl-acetaldehyde | nurse | Y | syringe 3/5/10 | 5 ml | |
| trimethyl-acetaldehyde | nurse | R | micropipette | 400 ul | |
| trimethyl-acetaldehyde | nurse | R | micropipette | 400 ul | |
| trimethyl-acetaldehyde | nurse | R | micropipette | 400 ul | |
| trimethyl-acetaldehyde | lemon | R | micropipette | 400 ul | |
| trimethyl-acetaldehyde | lemon | R | micropipette | 400 ul | |
| trimethyl-acetaldehyde | lemon | R | micropipette | 400 ul | |

In combination with the data from Examples 1 and 3, which demonstrate the repellent activity of valeraldehyde and 3-methylbutanal, both five carbon aldehydes, the data demonstrate the repellent activity of aldehydes with saturated carbon chains comprising 1 to about 6 carbons.

Tonic immobility studies were carried out using diethylacetaldehyde on juvenile lemon, juvenile nurse, blacktip and tiger sharks. In six of six Syringe 3/5/10 Assays, tonic immobility was terminated in juvenile nurse sharks. In two of four Syringe 3/5/10 Assays, tonic immobility was terminated in blacktip sharks. In one 3/5/10 Syringe Assay, a behavioral response was noted during tonic immobility. In one 3/5/10 Syringe Assay, no response was noted. In one 3/5/10 Syringe Assay on a tiger shark, tonic immobility was terminated.

In twelve Hd Syringe Assays on juvenile lemon and nurse sharks, a behavioral response during tonic immobility was observed in 9 assays. In three assays tonic immobility was fully terminated. In eight Micropipette Assays in juvenile lemon and nurse sharks a gustatory response was noted with two full terminations of tonic immobility. In two Micropipette Assays, no response was noted. See Table 20.

TABLE 20

Tonic Immobility Assays with Saturated C1-C6 Aldehydes

| Component | Species | T? | Delivery | Dose | Response | Comments |
|---|---|---|---|---|---|---|
| diethylacetaldehyde | nurse | Y | syringe 3/5/10 | 5 ml | 4 sec | |
| diethylacetaldehyde | nurse | Y | syringe 3/5/10 | 2.6 ml | 4 sec | |
| diethylacetaldehyde | nurse | Y | syringe 3/5/10 | 0.4 ml | 5 sec | |
| diethylacetaldehyde | nurse | Y | syringe 3/5/10 | 1 ml | 2 sec | |
| diethylacetaldehyde | nurse | Y | syringe 3/5/10 | 3.6 ml | 3 sec | |
| diethylacetaldehyde | nurse | Y | syringe 3/5/10 | 1.2 ml | 1 sec | |
| diethylacetaldehyde | blacktip | Y | syringe 3/5/10 | 6.5 ml | 5 sec | |
| diethylacetaldehyde | blacktip | Y | syringe 3/5/10 | 6 ml | 5 sec | |
| diethylacetaldehyde | blacktip | R | syringe 3/5/10 | 6 ml | 5 sec | cough/tensed |
| diethylacetaldehyde | blacktip | N | syringe 3/5/10 | 4.9 ml | | |
| diethylacetaldehyde | Tiger | Y | syringe 3/5/10 | 5.6 ml | 2.83 sec | 120 cm female tiger on Longline |
| diethylacetaldehyde | lemon | R | hd syringe | 1 ml | 1.86 sec | cough |
| diethylacetaldehyde | Lemon | R | hd syringe | 0.6 ml | | cough |
| diethylacetaldehyde | Lemon | R | hd syringe | 0.8 ml | | cough |
| diethylacetaldehyde | Lemon | R | hd syringe | 1.1 ml | | cough |
| diethylacetaldehyde | Lemon | R | hd syringe | 1.3 ml | | cough |
| diethylacetaldehyde | Lemon | R | hd syringe | 1.5 ml | | cough |
| diethylacetaldehyde | Lemon | Y | hd syringe | 1.5 ml | 5.96 sec | |
| diethylacetaldehyde | Nurse | R | hd syringe | 0.3 ml | 1.33 sec | cough |
| diethylacetaldehyde | Nurse | R | hd syringe | 0.4 ml | 3.23 sec | cough |
| diethylacetaldehyde | Nurse | Y | hd syringe | 1.2 ml | 5.62 sec | |
| diethylacetaldehyde | Nurse | R | hd syringe | 0.3 ml | 1.39 sec | cough |

TABLE 20-continued

Tonic Immobility Assays with Saturated C1-C6 Aldehydes

| Component | Species | T? | Delivery | Dose | Response | Comments |
|---|---|---|---|---|---|---|
| diethylacetaldehyde | Nurse | Y | hd syringe | 1.5 ml | 0.78 sec | |
| diethylacetaldehyde | lemon | R | micropipette | 300 ul | | blinked |
| diethylacetaldehyde | lemon | N | micropipette | 200 ul | | |
| diethylacetaldehyde | lemon | R | micropipette | 150 ul | | cough |
| diethylacetaldehyde | lemon | R | micropipette | 150 ul | | cough |
| diethylacetaldehyde | lemon | R | micropipette | 150 ul | | cough |
| diethylacetaldehyde | lemon | N | micropipette | 100 ul | | |
| diethylacetaldehyde | lemon | N | micropipette | 200 ul | | |
| diethylacetaldehyde | lemon | R | micropipette | 250 ul | | cough |
| diethylacetaldehyde | nurse | Y | micropipette | 270 ul | 1 sec | |
| diethylacetaldehyde | nurse | Y | micropipette | 270 ul | 1 sec | |
| diethylacetaldehyde | nurse | R | micropipette | 500 ul | | |

The data in Table 20 evidences the repellent activity of diethylacetaldehyde, further supporting the repellent activity of aldehydes with saturated carbon chains comprising 1 to about 6 carbons.

Example 5

Piperonal (Aromatic Aldehyde), Ionone (Ketone) or Zingerone (Ketone) Repellents on Free-Swimming Elasmobranchs A series of chemical repellent tests on free-swimming Caribbean reef sharks (C. perezii) and blacknose sharks (C. acronotus) was performed in tropical waters. A small metal cage containing bait was suspended below a float in the water column. A ⅜" ID HDPE diptube was secured from the cage to the boat, so that chemical compounds could be transported to the cage's proximity. Sharks were stimulated using bunker chum in bags.

Sharks were observed to immediately bump and bite at the cage. The number of interactions was recorded using an underwater pole-camera. When 500 mL of 50% w/w piperonal in diethylene glycol monoethyl ether was presented, the number of strikes was dramatically reduced, and interactions ceased. When 500 mL of 50% w/w alpha-ionone in diethylene glycol monoethyl ether was presented, the number of strikes was reduced, but interactions continued after a 10 minute period. When 500 mL of 50% w/w zingerone in diethylene glycol monoethyl ether was presented, the number of strikes was reduced, but interactions continued after a 10 minute period.

Example 6

Natural Aldehyde Elasmobranch Repellents

Tonic immobility studies were carried out on juvenile lemon and nurse sharks using natural aldehydes including trans-cinnimaldehyde, cuminaldehyde and a combination of natural aldehydes. Syringe, and Syringe 3/5/10 assays were carried out as described in Examples 1 and 2.

Two Syringe assays (one on a lemon shark the other on a nurse share) using trans-cinnimaldehyde resulted in termination of tonic immobility. One Syringe assay on a lemons shark using cuminaldehyde resulted in termination of tonic immobility.

A combination of natural aldehydes was created from 4.4 g cuminaldehyde (cumin) and 5.3 g mixed isomers of anisaldehyde (anise) solubilized in 19.8 g denatured ethanol. In one Syringe 3/5/10 Assay on a juvenile nurse shark, a behavioral response within tonic immobility was observed. In three other Syringe 3/5/10 Assays, no response was observed. See Table 21. In two of the negative response assays only 500 microliters of chemical was delivered to the shark. This may explain the lack of response. See Table 21.

TABLE 21

Tonic Immobility Assays with Natural Aldehydes

| Component | Species | T? | Delivery | Dose | Response |
|---|---|---|---|---|---|
| Trans-cinnimaldehyde | lemon | Y | syringe | 21 ml | 4.31 sec |
| trans-cinnimaldehyde | nurse | Y | syringe | 33 ml | 4.97 sec |
| cuminaldehyde | lemon | Y | syringe | 19 ml | 3.94 sec |
| natural aldehydes | nurse | R | syringe 3/5/10 | 6 ml | |
| natural aldehydes | nurse | N | syringe 3/5/10 | 6 ml | |
| natural aldehydes | nurse | N | syringe 3/5/10 | 500 ul | |
| natural aldehydes | nurse | N | syringe 3/5/10 | 500 ul | |

Together these data demonstrate the repellent activity of natural aldehydes including trans-cinnimaldehyde and cuminaldehyde.

Example 7

Aromatic Aldehyde Elasmobranch Repellents

Tonic immobility studies were carried out on juvenile lemon sharks, juvenile nurse sharks and a blacknose shark using aromatic aldehydes including a mixture of methoxy/vanillin (containing methoxybenzaldehydes and vanillin) and toluraldehyde. Syringe and Micropipette assays were carried out as described in Examples 1 and 2.

A methoxybenzaldehyde combination with vanillin was made from 2 g Ortho-vanillin, 1 g 2,4,5-trimethoxybenzaldehyde, 1 g 2,3,4-trihydroxybenzaldehyde, 1 g 3-hydroxy-4-methoxybenzaldehyde, 1 g 2,3,4-trimethoxybenzaldehyde, 1 g 2,5-dimethoxybenzaldehyde, 1 g veratraldehyde, 1 g 4-hydroxy-3-methoxybenzaldehyde, 1 g 3-ethoxy-4-hydroxy-benzaldehyde, and 50 g denatured alcohol.

Seven Syringe assays were carried out using the methoxy/vanillin repellent combination on lemon sharks, one Syringe assay was carried out on a blacknose shark and one Syringe assay was carried out on a nurse shark. Five of six assays on lemon shark resulted in termination of tonic immobility. One assay on a lemon shark resulted in a change in behavior during tonic immobility. One assay on a nurse shark had no response. One assay on a nurse shark was inconclusive because the shark became ill. The assay on the blacknose shark resulted in termination of tonic immobility. See Table 22. In six of ten Micropipette assays on lemon shark, a response was observed. This demonstrates that methoxy/vanillin is a gustatory repellent. See Table 22.

Using p-tolualdehyde, one Syringe Assay on a lemon shark resulted in termination of tonic immobility. See Table 22.

Using veratraldehyde, six of six Syringe Assays on lemon and nurse sharks resulted in termination of tonic immobility. See Table 22. In a single Syringe Assay on a nurse shark no response was observed. In eight of twelve Micropipette Assays a gustatory response was observed in lemon sharks. In four Micropipette assays, no response was observed.

anisal 68.075 g; mesityl oxide 29.445 g; p-tolualdehyde 36.045 g; and veratraldehyde 16.618 g. The combination was labeled BA1.

Tonic immobility studies were carried out with the aldehyde combination labeled BA1 on juvenile lemon sharks, juvenile nurse sharks and blacktip sharks using the above-described aldehyde mixture. Syringe, Syringe 3/5/10, Bite and Micropipette assays were carried out as described in Examples 1 and 2. In three Syringe and six Bite assays on juvenile nurse sharks all assays terminated tonic immobility. In three Syringe and one Syringe 3/5/10 assay on juvenile lemon sharks all assays terminated tonic immobility. In one

TABLE 22

Tonic Immobility Assays with Aromatic Aldehydes

| Component | Species | T? | Delivery | Dose | Response | Comments |
|---|---|---|---|---|---|---|
| methoxy/vanillin mixture | lemon | R | syringe | 27 ml | | |
| methoxy/vanillin mixture | nurse | N | syringe | 54 ml | | |
| methoxy/vanillin mixture | lemon | Y | syringe | 5 ml | 1.91 sec | |
| methoxy/vanillin mixture | lemon | Y | syringe | 14 ml | 4.72 sec | |
| methoxy/vanillin mixture | lemon | Y | syringe | 11 ml | 6.92 sec | |
| methoxy/vanillin mixture | nurse | N/A | syringe | 47 ml | | shark nearly dead, overdose of alcohol/aldehydes |
| methoxy/vanillin mixture | lemon | R | syringe | 6 ml | 2.4 sec | |
| methoxy/vanillin mixture | lemon | Y | syringe | 10 ml | 3.82 sec | |
| methoxy/vanillin mixture | lemon | Y | syringe | 16 ml | 5.2 sec | |
| methoxy/vanillin mixture | blacknose | Y | syringe | 50 ml | <20 sec | |
| methoxy/vanillin mixture | lemon | Y | micropipette | 100 ul | 5 sec | |
| methoxy/vanillin mixture | lemon | R | micropipette | 100 ul | 2 sec | |
| methoxy/vanillin mixture | lemon | N | micropipette | 100 ul | 8 sec | |
| methoxy/vanillin mixture | lemon | R | micropipette | 100 ul | 2 sec | |
| methoxy/vanillin mixture | lemon | R | micropipette | 23 ul | 10 sec | |
| methoxy/vanillin mixture | lemon | N | micropipette | 25 ul | | |
| methoxy/vanillin mixture | lemon | Y | micropipette | 300 ul | | |
| methoxy/vanillin mixture | lemon | Y | micropipette | 300 ul | | |
| methoxy/vanillin mixture | lemon | N | micropipette | 300 ul | | |
| methoxy/vanillin mixture | lemon | N | micropipette | 300 ul | | |
| p-tolualdehyde | lemon | Y | syringe | 22 ml | 3.54 sec | |
| veratraldehyde | lemon | Y | syringe | 16 ml | 2.67 sec | |
| veratraldehyde | lemon | Y | syringe | 20 ml | 6.45 sec | |
| veratraldehyde | lemon | Y | syringe | 10 ml | 1.06 sec | |
| veratraldehyde | lemon | Y | syringe | 11.5 ml | 0.94 sec | |
| veratraldehyde | nurse | Y | syringe | 4.5 ml | 0.54 sec | |
| veratraldehyde | nurse | Y | syringe | 29 ml | 9.71 sec | |
| veratraldehyde | nurse | N | syringe | 47 ml | | |
| veratraldehyde | lemon | R | micropipette | 100 ul | | |
| veratraldehyde | lemon | N | micropipette | 100 ul | | |
| veratraldehyde | lemon | R | micropipette | 100 ul | 3 sec | |
| veratraldehyde | lemon | N | micropipette | 100 ul | | |
| veratraldehyde | lemon | R | micropipette | 100 ul | 3 sec | |
| veratraldehyde | lemon | Y | micropipette | 100 ul | 12 sec | |
| veratraldehyde | lemon | N | micropipette | 250 ul | | |
| veratraldehyde | lemon | Y | micropipette | 100 ul | 3 sec | |
| veratraldehyde | lemon | N | micropipette | 250 ul | | |
| veratraldehyde | lemon | N | micropipette | 280 ul | | |
| veratraldehyde | lemon | Y | micropipette | 300 ul | 3 sec | |
| veratraldehyde | lemon | Y | micropipette | 280 ul | 2 sec | |
| veratraldehyde | lemon | Y | micropipette | 310 ul | 2 sec | |

Together these data evidence the gustatory repellent activity of aromatic aldehydes such as methoxy/vanillin, p-tolualdehyde and veratraldehyde.

Example 8

Longer Aldehydes and Combinations of Aldehydes

A combination of aldehydes was prepared in about 873 g of methanol in the following amounts: butanal 144.22 g; isobutanal 144.22 g; pentanal 172.26 g; hexanal 200.32 g; decanal 46.884 g; cuminal 44.463 g; cinnimal 52.864 g;

Syringe assay and one Syringe 3/5/10 assay on blacktip sharks both resulted in termination of tonic immobility. These data demonstrate the excellent repellent activity of the above-described mixture of aldehydes. See Table 23.

In one Micropipette assay in a juvenile lemon shark no response was observed. Nevertheless, because the aldehydes that have been combined to create the above-described aldehyde mixture have demonstrated gustatory stimulation in other Micropipette assays, it is concluded that the aldehyde mixture tested here is a gustatory repellent. See Table 23.

In a cloud dispersion assay, a population of competitively feed Caribbean reef and blacknose sharks was repelled from the feeding zone with a delivery of 500 mL of BA1 repellent composition.

A combination of aldehydes in the following amounts was prepared in about 1294 grams of methanol: proprional 174.24 g; butanal 216.33 g; isobutanal 216.33 g; pentanal 172.26 g; hexanal 100.16 g; heptanal 28.5475 g; octanal 64.11 g; nonanal 35.5625 g; decanal 78.14 g; cuminal 74.105 g; cinnimal 66.08 g; anisal 68.075 g; and mesityl oxide 29.445 g. The combination was labeled BA2.

Tonic immobility studies were carried out with the aldehyde combination labeled BA2 on juvenile lemon sharks using the above-described aldehyde combination. Syringe, and Micropipette Assays were carried out as described in Examples 1 and 2. Pipette Assays were carried out in the same manner as Micropipette Assays with delivery of the repellent directly to the mouth except the volumes were sometimes larger. In three of four Syringe Assays in lemon shark, tonic immobility was terminated. In one Syringe Assay, a behavioral change was observed within tonic immobility. In four of four Pipette Assays, tonic immobility in lemon sharks was terminated. In three Micropipette Assays a gustatory response was observed. In three others no response was observed.

A combination of aldehydes and a ketone in the following amounts was prepared in 160 grams of denatured alcohol: Butyraldehyde 10 g; Isobutyraldehyde 10 g; Veratraldehyde 10 g; and 2,3-butanedione (Diacetyl) 10 g. The combination was labeled BA3. A cloud dispersion of the repellent composition was delivered to a population of Caribbean reef and blacknose shark competitively feeding. The sharks were dispersed from the feeding zone. In one Syringe Assay with the BA3 repellent on a juvenile lemon shark, tonic immobility was terminated. In two other Syringe Assays (one on a lemon shark and one on a nurse shark) behavioral changes were observed within tonic immobility. In one additional Syringe Assay, a nurse shark experienced a violent seizure and the assay could not be finished.

A combination of aldehydes and ammonium acetate was prepared in the following amounts in 258 grams of denatured alcohol and 200 g of water: butyraldehyde 72.1 g; isobutyraldehyde 36.2 g; veratraldehyde 35.0 g; and ammonium acetate 50 g. The repellent composition was labeled BA4. In two cloud assays in free-swimming competitively feeding Caribbean reef and blacknose sharks, a cloud dispersion of 500 mL of the repellent composition BA4 repelled the sharks from the feeding zone.

TABLE 23

Tonic Immobility Assays with Aldehyde Mixture

| Component | Species | T? | Delivery | Dose | | Response | |
|---|---|---|---|---|---|---|---|
| Aldehyde mixture BA1 | nurse | Y | syringe | 4 | ml | 1.38 | sec |
| Aldehyde mixture BA1 | nurse | Y | syringe | 6 | ml | 3.41 | sec |
| Aldehyde mixture BA1 | lemon | Y | syringe | 5 | ml | 2.03 | sec |
| Aldehyde mixture BA1 | lemon | Y | syringe | 9 | ml | 4.09 | sec |
| Aldehyde mixture BA1 | lemon | Y | syringe | 5 | ml | 2.72 | sec |
| Aldehyde mixture BA1 | nurse | Y | syringe | 9 | ml | 4.60 | sec |
| Aldehyde mixture BA1 | blacktip | Y | syringe | 20 | ml | | |
| Aldehyde mixture BA1 | lemon | Y | syringe 3/5/10 | 6 | ml | 5 | sec |
| Aldehyde mixture BA1 | blacktip | Y | syringe 3/5/10 | 6 | ml | 5 | sec |
| Aldehyde mixture BA1 | nurse | Y | bite | 5 | ml | | |
| Aldehyde mixture BA1 | nurse | Y | bite | 5 | ml | | |
| Aldehyde mixture BA1 | nurse | Y | bite | 5 | ml | | |
| Aldehyde mixture BA1 | nurse | Y | bite | 2 | ml | 1 | sec |
| Aldehyde mixture BA1 | nurse | Y | bite | 2 | ml | 1 | sec |
| Aldehyde mixture BA1 | nurse | Y | bite | 2 | ml | 1 | sec |
| Aldehyde mixture BA1 | lemon | N | micropipette | 500 | ul | | |
| aldehyde mixture BA1 | carib reef/black nose | Y | cloud - co2 | 500 | mL | | |
| aldehyde mixture BA2 | lemon | Y | syringe | 9 | ml | 3.48 | sec |
| aldehyde mixture BA2 | lemon | R | syringe | 15 | ml | 7.49 | sec |
| aldehyde mixture BA2 | lemon | Y | syringe | 13 | ml | 2.99 | sec |
| aldehyde mixture BA2 | lemon | Y | syringe | 5 | ml | 5.30 | sec |
| aldehyde mixture BA2 | lemon | Y | pipette | 1 | ml | | |
| aldehyde mixture BA2 | lemon | Y | pipette | 0.5 | ml | 2.98 | sec |
| aldehyde mixture BA2 | lemon | Y | pipette | 0.5 | ml | | |
| aldehyde mixture BA2 | lemon | Y | pipette | >0.5 | ml | | |
| aldehyde mixture BA2 | lemon | N | micropipette | 25 | ul | | |
| aldehyde mixture BA2 | lemon | R | micropipette | 25 | ul | | |
| aldehyde mixture BA2 | lemon | R | micropipette | 18 | ul | | |
| aldehyde mixture BA2 | lemon | N | micropipette | 10 | ul | | |
| aldehyde mixture BA2 | lemon | N | micropipette | 10 | ul | | |
| aldehyde mixture BA2 | lemon | R | micropipette | 25 | ul | | |
| aldehyde mixture BA3 | carib reef/ blacknose | Y | cloud | 1000 | ul | | |
| aldehyde mixture BA3 | lemon | Y | syringe | 25 | ml | 8 | sec |
| aldehyde mixture BA3 | nurse | R | syringe | 60 | ml | 5 | sec |
| aldehyde mixture BA3 | lemon | R | syringe | 27 | ml | | |
| aldehyde mixture BA3 | nurse | N/A | syringe | 100 | mL | Violent Seizure | |
| aldehyde mixture BA4 | carib reef/ blacknose | R | cloud - co2 | 500 | mL | | |
| aldehyde mixture BA4 | carib reef/ blacknose | R | cloud - co2 | 500 | mL | | |
| octanal | lemon | Y | syringe | 37 | ml | 6.23 | sec |

TABLE 23-continued

Tonic Immobility Assays with Aldehyde Mixture

| Component | Species | T? | Delivery | Dose | Response |
|---|---|---|---|---|---|
| nonanal | lemon | Y | syringe | 30 ml | 5.00 sec |
| decanal | nurse | Y | syringe | 60 ml | 17.72 sec |
| heptanal | lemon | N | syringe | 56 ml | |
| mesityl oxide | lemon | Y | syringe | 38 ml | 6.21 sec |

Some of the longer carbon chain aldehydes that had been included in the above-described aldehyde mixture were also tested for repellent activity.

In Syringe assays on lemon sharks using octanal, nonanal and mesityl oxide, tonic immobility was terminated. In a Syringe assay on a nurse shark using decanal tonic immobility was terminated. In a Syringe assay on a lemon shark using heptanal, no response was observed. This lack of response may have resulted from an unfavorable water current.

Example 9

Carboxylic Acid Elasmobranch Repellents

A wide range of carboxylic acids was tested on lemon, nurse, blacktip, blacknose, tiger and great hammerhead sharks. The carboxylic acids listed in Table 9 were each tested. Further, a range of doses of the following components were tested: cinnamic acid; citric acid; crotonic acid; lactic acid; aqueous succinic acid; crotonic acid, cinnamic acid, and maleic acid in glycol; and crotonic acid, citric acid and fumaric acid in solution. See Table 24. All compositions evidenced repellent characteristics.

The results together demonstrate the effective repellent characteristics of carboxylic acid compositions. Tonic immobility studies were carried out on many different carboxylic acids as well as cloud dispersal studies in free-swimming individual sharks. The data demonstrate the repellent activity of carboxylic acids.

In a first set of studies on the effectiveness of carboxylic acids as elasmobranch repellents, each tested substance was subjected to the following protocol. In a first micropipette assay on a juvenile lemon shark, an oral dose of no more than 100 microliters of carboxylic acid was observed to terminate tonic immobility. An oral dose of no more than 400 microliters was then delivered by micropipette into the mouth of a juvenile nurse shark. Tonic immobility was terminated. For butyric acid, each derivative of butyric acid and each naturally occurring acid listed in Table 9, the protocol was successfully repeated and each treatment resulted in termination of tonic immobility for each listed substance. The data evidences the gustatory repelling activity of carboxylic acids.

Further studies on carboxylic acids and mixtures of carboxylic acids were pursued. The data is contained in Table 24.

In four of four Hd Syringe assays, citric acid between 0.3 mL and 2.4 mL of citric acid 50% w/w was delivered about three inches from the mouth of a lemon shark. Each assay terminated tonic immobility. Seven Syringe 3/5/10 assays on nurse and lemons sharks were employed with crotonic acid solution. In four of the seven assays the crotonic acid was delivered directly to the mouth on a longline or within 10 inches of the shark's mouth. Tonic immobility was terminated. In one of the seven assays, the crotonic acid was delivered directly to the mouth of the shark on a longline and a behavioral response was observed in tonic immobility. In two of the seven assays, 6 mL of crotonic acid was delivered to lemon sharks at a distance of 36 inches from the shark's mouth. No response was observed. The lack of response is explained by the small volume delivered at a very large distance. See Table 24.

In two of three Syringe 3/5/10 assays, lactic acid was delivered to lemon sharks and terminated tonic immobility. In a single Syringe 3/5/10 assay, lactic acid was delivered to a lemon shark and no behavioral change was observed. See Table 24.

Crotonic Acid (25.0 g), Cinnamic Acid (10.0 g) and Maleic Acid (25.0 g) were combined in 100.0 g Diethyl Glycol Monoethyl Ether to create a repellent composition. In three of four Syringe 3/5/10 assays, the repellent carboxylic acid composition (crotonic/cinnamic/maleic) was delivered to tiger and blacknose sharks and terminated tonic immobility. In one of four Syringe 3/5/10 assays, delivery of the repellent actually missed the mouth of the shark and only a behavior change was seen in tonic immobility. See Table 24.

In a cloud dispersal assay 400 ml of the carboxylic acid composition (crotonic/cinnamic/maleic) was dispersed from a diptube near the mouth of a great hammerhead shark. The shark fled the area and did not return. See Table 24.

TABLE 24

Tonic Immobility Assays with Carboxylic Acids

| Component | Species | T? | Delivery | Dose | Response | Comments |
|---|---|---|---|---|---|---|
| cinnamic acid solution | lemon | N | syringe 3/5/10 | 1.5 ml | | mouth |
| citric acid 50% w/w | lemon | Y | hd syringe | 2.4 ml | | both |
| citric acid 50% w/w | lemon | Y | hd syringe | 2.5 ml | | both |
| citric acid 50% w/w | lemon | Y | hd syringe | 0.3 ml | | both |
| citric acid 50% w/w | lemon | Y | hd syringe | 1.5 ml | | mouth |
| citric acid 50% w/w | lemon | Y | syringe 3/5/10 | 6 ml | | mouth longline/231 cm |
| citric acid 50% w/w | lemon | Y | syringe 3/5/10 | 2 ml | | mouth |
| citric acid 50% w/w | lemon | N | syringe 3/5/10 | 2.5 ml | | distanced 6 inches |
| citric acid 50% w/w | lemon | Y | syringe 3/5/10 | 6 ml | | distanced 12 inches |
| citric acid 50% w/w | lemon | N | syringe 3/5/10 | 6 ml | | distanced 12 inches |
| citric acid 50% w/w | lemon | N | syringe 3/5/10 | 6 ml | | distanced 10 inches |

TABLE 24-continued

Tonic Immobility Assays with Carboxylic Acids

| Component | Species | T? | Delivery | Dose | Response | Comments |
|---|---|---|---|---|---|---|
| citric acid 50% w/w | lemon | Y | syringe 3/5/10 | 6 ml | | distanced longline |
| citric acid 50% w/w | lemon | N | syringe 3/5/10 | 6 ml | | mouth longline |
| citric acid 50% w/w | lemon | R | syringe 3/5/10 | 6 ml | | mouth longline |
| citric acid 50% w/w | nurse | R | syringe 3/5/10 | 6 ml | | mouth longline/3 coughs |
| citric acid 50% w/w | nurse | R | syringe 3/5/10 | 6 ml | | mouth longline |
| citric acid 50% w/w | blacktip | Y | syringe 3/5/10 | 6 ml | | mouth longline |
| citric acid 50% w/w | blacknose | R | syringe 3/5/10 | 6 ml | | both longlinge/cough |
| citric acid 50% w/w | blacknose | Y | syringe 3/5/10 | 6 ml | | mouth |
| crotonic acid solution | lemon | Y | syringe 3/5/10 | 6 ml | | distanced |
| crotonic acid solution | nurse | Y | syringe 3/5/10 | 6 ml | | mouth |
| crotonic acid solution | nurse | R | syringe 3/5/10 | 6 ml | | mouth longline/cough |
| crotonic acid solution | lemon | Y | syringe 3/5/10 | 6 ml | | mouth longline/231 cm |
| crotonic acid solution | lemon | Y | syringe 3/5/10 | 6 ml | | distanced 10 inches |
| crotonic acid solution | lemon | N | syringe 3/5/10 | 6 ml | | distanced 36 inches |
| crotonic acid solution | lemon | N | syringe 3/5/10 | 6 ml | | distanced 36 inches |
| lactic acid | lemon | N | syringe 3/5/10 | 1.5 ml | | mouth |
| lactic acid | lemon | Y | syringe 3/5/10 | 1.5 ml | | r nare |
| lactic acid | lemon | Y | syringe 3/5/10 | 0.5 ml | | mouth |
| saturated succinic acid solution aq | lemon | R | micropipette | 400 ul | | mouth |
| saturated succinic acid solution aq | lemon | R | micropipette | 400 ul | | left nare |
| succinic acid | lemon | N | swab | | | |
| succinic acid | lemon | N | swab | | | |
| crotonic/cinnamic/maleic in glycol | tiger | Y | syringe 3/5/10 | 5 ml | | mouth violent |
| crotonic/cinnamic/maleic in glycol | blacknose | Y | syringe 3/5/10 | 5 ml | | mouth |
| crotonic/cinnamic/maleic in glycol | tiger | R | syringe 3/5/10 | 5 ml | | mouth missed mouth, plumed |
| crotonic/cinnamic/maleic in glycol | tiger | Y | syringe 3/5/10 | 5 ml | | mouth |
| crotonic/cinnamic/maleic in glycol | great hammerhead | Y | diptube to bait | 400 ml | | poss mouth 13' hammerhead at mini-barge, did not return |
| crotonic/citric/fumaric solution | nurse | R | syringe 3/5/10 | 6 ml | | mouth longline/cough |
| crotonic/citric/fumaric solution | lemon | Y | syringe 3/5/10 | 0.5 ml | | both |
| crotonic/citric/fumaric solution | lemon | Y | syringe 3/5/10 | 6 ml | | distanced 36 inches/shark moved into cloud |
| crotonic/citric/fumaric solution | nurse | Y | syringe 3/5/10 | 6 ml | | mouth |
| crotonic/citric/fumaric solution | lemon | Y | syringe 3/5/10 | 6 ml | | mouth very large specimen in pen |
| crotonic/citric/fumaric solution | lemon | Y | syringe 3/5/10 | 6 ml | | mouth longline |
| crotonic/citric/fumaric solution | nurse | Y | syringe 3/5/10 | 6 ml | | mouth longline |
| crotonic/citric/fumaric solution | nurse | Y | micropipette | 200 ul | | mouth spit |
| crotonic/citric/fumaric solution | lemon | Y | micropipette | 300 ul | | mouth |
| crotonic/citric/fumaric solution | lemon | Y | micropipette | 215 ul | | mouth |
| crotonic/citric/fumaric solution | lemon | Y | micropipette | 120 ul | | mouth |
| crotonic/citric/fumaric solution | lemon | Y | micropipette | 100 ul | | mouth |
| crotonic/citric/fumaric solution | lemon | Y | micropipette | 100 ul | | mouth |
| crotonic/citric/fumaric solution | lemon | Y | micropipette | 100 ul | | mouth |
| crotonic/citric/fumaric solution | lemon | Y | micropipette | 200 ul | | mouth |
| crotonic/citric/fumaric solution | lemon | Y | micropipette | 200 ul | | mouth |
| crotonic/citric/fumaric solution | lemon | Y | micropipette | 150 ul | | mouth |
| crotonic/citric/fumaric solution | lemon | Y | micropipette | 125 ul | | mouth |
| crotonic/citric/fumaric solution | lemon | Y | micropipette | 125 ul | | mouth |
| crotonic/citric/fumaric solution | lemon | Y | micropipette | 100 ul | | mouth |
| crotonic/citric/fumaric solution | lemon | Y | micropipette | 100 ul | | mouth |

TABLE 24-continued

Tonic Immobility Assays with Carboxylic Acids

| Component | Species | T? | Delivery | Dose | Response | Comments |
|---|---|---|---|---|---|---|
| crotonic/citric/fumaric solution | lemon | Y | micropipette | 50 ul | | mouth |
| crotonic/citric/fumaric solution | lemon | Y | micropipette | 50 ul | | mouth |
| crotonic/citric/fumaric solution | nurse | R | micropipette | 300 ul | | mouth |
| crotonic/citric/fumaric solution | nurse | R | micropipette | 300 ul | | mouth spit |
| crotonic/citric/fumaric solution | nurse | R | micropipette | 300 ul | | mouth |
| crotonic/citric/fumaric solution | nurse | Y | micropipette | 200 ul | | mouth |
| crotonic/citric/fumaric solution | nurse | Y | micropipette | 100 ul | | mouth |
| crotonic/citric/fumaric solution | nurse | Y | micropipette | 100 ul | | mouth |
| crotonic/citric/fumaric solution | nurse | Y | micropipette | 50 ul | | r nare |
| crotonic/citric/fumaric solution | nurse | Y | micropipette | 50 ul | | r nare |
| crotonic/citric/fumaric solution | nurse | R | micropipette | 50 ul | | l nare cough |
| crotonic/citric/fumaric solution | nurse | R | micropipette | 25 ul | | r nare |
| crotonic/citric/fumaric solution | nurse | R | micropipette | 25 ul | | r nare cough |

In a surrounding cloud dispersal assay, 500 mL of a mixture of 20% w/w Crotonic acid, 10% w/w Citric acid and 5% w/w Cinnamic acid solubilized in 50:50 w/w water:ethanol was delivered in a subsurface dose in the vicinity of a population of competitively feed sharks (5 Caribbean reef sharks and 2 blacknose sharks). The sharks were dispersed and did not return.

Together, these data evidence the effectiveness of carboxylic acids and combinations of carboxylic acids as elasmobranch repellents.

Example 10

Pyridine Elasmobranch Repellents

Tonic immobility studies were carried out on juvenile lemon sharks and juvenile nurse sharks using 100% pyridine, 100% 3-methylpyridine and 100% 2-amino-3-picoline at 95% or 2-amino-3-picoline 95% cut to 10% w/w in desalinated water. Syringe 3/5/10, Hd Syringe and Micropipette assays were carried out as described in Examples 1 and 2. In three Syringe and six Bite assays on juvenile nurse sharks all assays terminated tonic immobility. In three Syringe and one Syringe 3/5/10 assay on juvenile lemon sharks all assays terminated tonic immobility. In one Syringe assay and one Syringe 3/5/10 assay on blacktip sharks both resulted in termination of tonic immobility. In one cloud dispersion assay with 2-amino-3-picoline 95% cut to 10% w/w with desalinated water, Caribbean reef sharks demonstrated a population decrease upon the administration of 500 mL of repellent. See Table 25.

TABLE 25

Tonic Immobility Assays with Pyridine

| Component | Species | T? | Delivery | Dose | Response | Comments |
|---|---|---|---|---|---|---|
| Pyridine | nurse | Y | syringe 3/5/10 | 5.7 ml | 2 sec | |
| Pyridine | nurse | R | syringe 3/5/10 | 6 ml | | |
| Pyridine | lemon | Y | syringe 3/5/10 | 1.2 ml | 6 sec | |
| Pyridine | lemon | Y | syringe 3/5/10 | 3 ml | 5 sec | |
| Pyridine | nurse | N | micropipette | 500 ul | | |
| Pyridine | nurse | N | micropipette | 500 ul | | |
| 3-methylpyridine | lemon | Y | hd syringe | 0.7 ml | | |
| 3-methylpyridine | lemon | Y | hd syringe | 0.3 ml | | |
| 3-methylpyridine | nurse | Y | hd syringe | 0.7 ml | | |
| 2-amino-3-picoline 95% | lemon | Y | micropipette | 400 ul | | mouth |
| 2-amino-3-picoline 95% | lemon | F | micropipette | 400 ul | | left nare - EXTREMELY VIOLENT/SEIZURE RESPONSE |
| 2-amino-3-picoline 95% cut to 10% w/w in desalinated water, TV = 500 mL | Caribbean reef | Y | cloud - co2 | 500 mL | | population decreased |

Together, the data in Table 25 evidence the effective gustatory repellent activity of pyridines and pyridine derivatives.

Example 11

Anti-Pyrine Elasmobranch Repellents

Compositions for repelling an elasmobranch comprising an anti-pyrine or a derivative thereof including anti-pyrine or 4-amino-antipyrine were tested. Tonic immobility studies were carried out on juvenile lemon sharks and juvenile nurse sharks using 4-aminoantipyrine and antipyrine solution. See Table 26. The 4-aminoantipyrine solution was prepared from 5 g 4-aminoantipyrine and 30 g water.

Hd Syringe, Syringe 3/5/10 and Micropipette assays were carried out as described in Examples 1 and 2. In four Hd Syringe assays on juvenile lemon sharks using 4-aminoantipyrines, all assays terminated tonic immobility. In one Hd Syringe assay on a juvenile nurse shark, tonic immobility was terminated even with a volume of 300 microliters. In only one Syringe 3/5/10 Assay on a blacktip shark, no response was observed using 4-aminoantipyrine. In one Micropipette assay on a juvenile lemon shark using antipyrine solution, a response was observed within tonic immobility. Together, these data evidence that antipyrine is a gustatory stimulant. In another Micropipette assay on a juvenile lemon shark, no response was noted.

TABLE 26

Tonic Immobility Assays with Antipyrine

| Component | Species | T? | Delivery | Dose |
|---|---|---|---|---|
| 4-aminoantipyrine | lemon | Y | hd syringe | 1.05 ml |
| 4-aminoantipyrine | lemon | Y | hd syringe | 0.45 ml |
| 4-aminoantipyrine | nurse | Y | hd syringe | 0.3 ml |
| 4-aminoantipyrine | lemon | Y | hd syringe | 0.5 ml |
| 4-aminoantipyrine | lemon | Y | hd syringe | 0.7 ml |
| 4-aminoantipyrine | blacktip | N | syringe 3/5/10 | 6 ml |
| antipyrine solution | lemon | R | micropipette | 400 ul |
| antipyrine solution | lemon | N | micropipette | 400 ul |

Example 12

Repellent Activity on Blue Sharks

In two assays each on two different blue sharks, 3-methylbutanal in dosages of 20 mL or less produced a behavioral response (classic mouth-agape response) from a direct delivery of the repellent to the mouth using a syringe. The sharks had been captured on rod and reel and were held in tonic immobility along a boat. The first shark had a total length of 6.5 feet. The second shark had a total length of 8 feet.

Example 13

Di-Ketones (Diacetyl) Elasmobranch Repellents

Di-ketones were tested for repellent activity on elasmobranchs. 2,3-butanedione evidenced a flight response in lemon and nurse sharks. See Table 27. The results, in combination with the results for ionone and zingerone on free-swimming sharks in Example 5 above, evidence the repellent activity of ketones and di-ketones. Tonic immobility studies were carried out on 2,3-butanedione and diacetyl in denatured alcohol. In seven of eight Syringe Assays, tonic immobility was terminated in juvenile lemon and nurse sharks. In one Syringe Assay, a behavioral response was noted during tonic immobility. In one cloud dispersion assay in free-swimming Caribbean reef and blacknose sharks, no response was noted since the volume was only 290 microliters. No response would be expected with such a low volume. In one bite assay with a juvenile nurse shark tonic immobility was terminated.

TABLE 27

Tonic Immobility Assays with Acetyl

| Component | Species | T? | Delivery | Dose | Response |
|---|---|---|---|---|---|
| 2,3-Butanedione (diacetyl) | lemon | Y | syringe | 10 ml | 3.34 sec |
| 2,3-Butanedione (diacetyl) | lemon | Y | syringe | 6 ml | 3.34 sec |
| 2,3-Butanedione (diacetyl) | lemon | Y | syringe | 2 ml | 2.43 sec |
| 2,3-Butanedione (diacetyl) | lemon | Y | syringe | 5 ml | 3.56 sec |
| 2,3-Butanedione (diacetyl) | nurse | Y | bite | 3 ml | |
| diacetyl | nurse | Y | syringe | 57 ml | 11.14 sec |
| diacetyl/SLX solution | carib reef/ blacknose | N | cloud - co2 | 290 ul | |
| diacetyl/SLX solution | nurse | R | syringe | 45 ml | |
| diacetyl mixture | lemon | Y | syringe | 7 ml | 1.52 sec |
| diacetyl mixture | lemon | Y | syringe | 6 ml | 1.40 sec |

Together with the data provided in Example 5 for ionone and zingerone, the data in Table 27 evidence the repellent activity of ketones and di-ketones.

What is claimed is:

1. An elasmobranch repellent comprising:
   (i) an aldehyde or a derivative thereof, a ketone or derivative thereof, a di-ketone or a derivative thereof, a pyridine or a derivative thereof, or an antipyrine or a derivative thereof, separately or in combination, wherein an effective amount of said aldehyde or a derivative thereof, ketone or derivative thereof, di-ketone or a derivative thereof, pyridine or derivative thereof, or antipyrine or derivative thereof, separately or in combination is capable of terminating tonic immobility of a tonic-immobile elasmobranch upon exposure to gustatory receptors of said elasmobranch; and
   (ii) an acceptable solvent, carrier and/or diluent.

2. The repellent of claim 1, wherein said aldehyde or derivative thereof is selected from the group consisting of 3-methylbutanal, 2-methylbutanal, 3-methylbutenal, 2-methylbutenal, valeraldehyde, trans-pentenal, propionaldehyde, butyraldehyde, isobutyraldehyde, capronaldehyde, trimethylacetaldehyde, trans-cinimaldehyde, cuminaldehyde, a methoxybenzaldehyde, 2-ethylbutyraldehyde, isobutyraldehyde, heptanal, octanal, nonanal, decanal, a dimethylbenzaldehyde, o-anisaldehyde, m-anisaldehyde and p-anisaldehyde, separately or in combination.

3. The repellent of claim 1, wherein said ketone or derivative thereof is selected from the group consisting of ionone and zingerone, separately or in combination.

4. The repellent of claim 1, wherein said di-ketone or derivative thereof is selected from the group consisting of 2,3-butanedione, glyoxal and methylglyoxal, separately or in combination.

5. The repellent of claim 1, wherein said pyridine or derivative thereof is selected from the group consisting of pyridine, 2-methylpyridine, 3-methylpyridine, 4-methylpyridine, lutidine, isomers of lutidine, collidine, isomers of collidine, and 2-amino-3-picoline, separately or in combination.

6. The repellent of claim 1, wherein said anti-pyrine or derivative thereof is selected from the group consisting of anti-pyrine or 4-amino-antipyrine, separately or in combination.

7. The repellent of claim 1, wherein said combination is selected from the group consisting of cuminaldehyde and anisaldehyde; the group consisting of butyraldehyde, isobutyraldehyde, veratraldehyde and 2,3-butanedione; the group consisting of butyraldehyde, isobutyraldehyde and veratraldehyde; and the group consisting of vanillin, 2,4,5-trimethoxybenzaldehyde, 2,3,4-trihydroxybenzaldehyde, 3-hydroxy-4-methoxybenzaldehyde, 2,3,4-trimethoxybenzaldehyde, 2,5-dimethoxybenzaldehyde, Veratraldehyde, 4-hydroxy-3-methoxybenzaldehyde and 3-ethoxy-4-hydroxy-benzaldehyde, separately or in combination.

8. The repellent of claim 1, wherein said aldehyde or derivative thereof is vanillin.

9. A method of repelling an elasmobranch comprising administering a composition for repelling an elasmobranch comprising an aldehyde or a derivative thereof, a ketone or derivative thereof, a di-ketone or derivative thereof, a pyridine or a derivative thereof, or an antipyrine or a derivative thereof, separately or in combination, in the expected proximity of said elasmobranch.

10. The method of claim 9 wherein said composition is administered from an aerosol container.

11. The method of claim 9, wherein said composition is administered in proximity of a longline.

12. A method of manufacturing an elasmobranch repellent comprising the steps of combining an aldehyde or a derivative thereof, a ketone or derivative thereof, a di-ketone or derivative thereof, a pyridine or a derivative thereof, or an antipyrine or a derivative thereof, separately or in combination, with an acceptable solvent, carrier or diluent.

13. A kit comprising a composition for repelling an elasmobranch comprising an aldehyde or a derivative thereof, a ketone or a derivative thereof, a di-ketone or a derivative thereof, a pyridine or a derivative thereof, or an antipyrine or a derivative thereof, separately or in combination, and a vehicle of administering said composition wherein said vehicle is selected from the group consisting of a pressurized or pressurizable delivery device, a pressurized or pressurizable repellent gun, a miniature pressurizable repellent gun to be worn on a wrist or an ankle of a subject, a spear fishing gun with an adjacent pressurizable repellent container, a time release sponge, a surfboard, a pump delivery system affixed to a surfboard, a pressurized delivery device affixed to a surfboard, a wristwatch comprising said repellent, a syringe, a pressurized syringe, an aerosol bomb, an aerosol bomb, a remote-controlled buoy with a repellent tank, a fixed buoy with a metering pump, a repellent pouch, a jelly comprising glycol ether and hydroxypropylcelluose, a porous fabric impregnated with repellent, rechargeable porous fabric impregnated with said repellent, a submerged repellent mine, a repellent-impregnated cable insulation for an undersea cable, and a repellent-impregnated cable jacket for an undersea cable.

14. A kit comprising a composition for repelling an elasmobranch comprising an aldehyde or a derivative thereof, a ketone or a derivative thereof, a di-ketone or a derivative thereof, a pyridine or a derivative thereof, or an antipyrine or a derivative thereof, separately or in combination, and a vehicle of administering said composition wherein said vehicle is a skin lotion containing said repellent.

15. The kit of claim 13, wherein said vehicle is an aerosol bomb.

* * * * *